US008551766B2

(12) United States Patent
Becker et al.

(10) Patent No.: US 8,551,766 B2
(45) Date of Patent: Oct. 8, 2013

(54) METHODS AND COMPOSITIONS TO DETECT NUCLEIC ACIDS IN A BIOLOGICAL SAMPLE

(75) Inventors: Michael M. Becker, San Diego, CA (US); Mehrdad R. Majlessi, Escondido, CA (US)

(73) Assignee: Gen-Probe Incorporated, San Diego, CA (US)

( * ) Notice: Subject to any disclaimer, the term of this patent is extended or adjusted under 35 U.S.C. 154(b) by 334 days.

(21) Appl. No.: 12/845,640

(22) Filed: Jul. 28, 2010

(65) Prior Publication Data

US 2012/0231551 A1    Sep. 13, 2012

Related U.S. Application Data

(62) Division of application No. 11/173,915, filed on Jun. 29, 2005, now Pat. No. 8,034,554.

(60) Provisional application No. 60/585,421, filed on Jul. 1, 2004.

(51) Int. Cl.
  C12Q 1/68 (2006.01)
  C12M 1/34 (2006.01)
  C12M 3/00 (2006.01)
  B01L 3/00 (2006.01)
  G01N 31/22 (2006.01)
  G01N 33/52 (2006.01)
  C07H 21/02 (2006.01)
  C07H 21/04 (2006.01)

(52) U.S. Cl.
  USPC ........ 435/287.2; 435/6.1; 435/6.11; 422/430; 536/23.1; 536/24.3

(58) Field of Classification Search
  USPC ..... 435/6.1, 6.11, 287.2; 422/430; 536/23.1, 536/24.3
  See application file for complete search history.

(56) References Cited

U.S. PATENT DOCUMENTS

| | | | |
|---|---|---|---|
| 4,174,384 A | 11/1979 | Ullman et al. | |
| 4,486,539 A | 12/1984 | Ranki et al. | |
| 4,556,643 A | 12/1985 | Paau et al. | |
| 4,725,536 A | 2/1988 | Fritsch et al. | |
| 4,752,566 A | 6/1988 | Collins et al. | |
| 4,766,062 A | 8/1988 | Diamond et al. | |
| 4,818,680 A | 4/1989 | Collins et al. | |
| 4,824,776 A | 4/1989 | Heller | |
| 4,894,325 A | 1/1990 | Englehardt et al. | |
| 5,118,801 A | 6/1992 | Lizardi et al. | |
| 5,124,246 A | 6/1992 | Urdea et al. | |
| 5,268,266 A | 12/1993 | Fritsch et al. | |
| 5,283,174 A * | 2/1994 | Arnold et al. | ................ 435/6.12 |
| 5,288,609 A | 2/1994 | Engelhardt et al. | |
| 5,312,728 A | 5/1994 | Lizardi et al. | |
| 5,439,793 A | 8/1995 | Rose et al. | |
| 5,445,933 A | 8/1995 | Eadie et al. | |
| 5,457,025 A | 10/1995 | Collins et al. | |
| 5,514,546 A | 5/1996 | Kool | |
| 5,607,834 A | 3/1997 | Bagwell | |
| 5,631,148 A | 5/1997 | Urdea | |
| 5,681,697 A | 10/1997 | Urdea et al. | |
| 5,702,893 A | 12/1997 | Urdea et al. | |
| 5,702,896 A | 12/1997 | Collins et al. | |
| 5,714,380 A | 2/1998 | Neri et al. | |
| 5,723,591 A | 3/1998 | Livak et al. | |
| 5,731,148 A | 3/1998 | Becker et al. | |
| 5,759,777 A | 6/1998 | Kearney et al. | |
| 5,780,224 A | 7/1998 | Collins | |
| 5,827,649 A | 10/1998 | Rose et al. | |
| 5,849,481 A | 12/1998 | Urdea et al. | |
| 5,861,273 A | 1/1999 | Olson et al. | |
| 5,914,230 A | 6/1999 | Liu et al. | |
| 5,925,517 A | 7/1999 | Tyagi et al. | |
| 6,025,133 A | 2/2000 | Stull et al. | |
| 6,030,787 A | 2/2000 | Livak et al. | |

(Continued)

FOREIGN PATENT DOCUMENTS

EP    0 070 685 A2    1/1983
EP    0 229 943 A2    7/1987

(Continued)

OTHER PUBLICATIONS

Ahern, Biochemical, Reagents Kits Offer Scientists Good Return on Investment, 1995, The Scientist 9(15):20, pp. 1-7.*
Examiner's Report, Canadian Patent Application No. 2,572,472, mailed Feb. 1, 2012.
Notice of Reason for Rejection, Japanese Patent Application No. 2007-520409, mailed Jan. 23, 2012.
USPTO Office Action, U.S. Appl. No. 12/845,640, mailed Mar. 15, 2012.
Krichevsky et al., A microRNA array reveals extensive regulation of microRNAs during brain development, RNA, 2003, 9: 1274-1281.
Written Opinion of the International Searching Authority for PCT/US2005/023555 dated Feb. 1, 2006.
International Search Report for PCT/US2005/023555 dated Feb. 1, 2006.
International Search Report and Written Opinion for PCT/US2005/023555 dated Feb. 14, 2006.

(Continued)

*Primary Examiner* — Narayan Bhat
(74) *Attorney, Agent, or Firm* — Jeffrey E. Landes

(57) ABSTRACT

Kits, reaction mixtures and methods for separating a target nucleic acid from a sample by using at least one hairpin capture probe oligonucleotide that has the structure 5'-X$_n$ a' b' c' Y$_n$-3', wherein X and Y each comprise nucleic acid sequences that can form a double stranded stem portion, one of X or Y is a capture sequence that is a first member of a specific binding pair and the other of X or Y is a terminal sequence of the hairpin capture probe, and a' b' c' comprises a target-complementary sequence flanked by X and Y to thereby form a loop portion of the hairpin, thus forming a capture hybrid that is separated from other sample components before the target nucleic acid is released from the capture support and hybridized to a detection probe that hybridizes specifically to the same sequence that is at least partially hybridized by the a' b' c' portion of the capture probe, thus forming a detectable detection hybrid to indicate the presence of the target nucleic acid in the sample.

23 Claims, 3 Drawing Sheets

(56) References Cited

U.S. PATENT DOCUMENTS

| | | | |
|---|---|---|---|
| 6,110,678 A | | 8/2000 | Weisburg et al. |
| 6,129,828 A | * | 10/2000 | Sheldon et al. ............... 204/518 |
| 6,130,038 A | * | 10/2000 | Becker et al. .................. 435/6.1 |
| 6,150,097 A | | 11/2000 | Tyagi et al. |
| 6,156,501 A | | 12/2000 | McGall et al. |
| 6,221,581 B1 | | 4/2001 | Engelhardt et al. |
| 6,268,128 B1 | | 7/2001 | Collins et al. |
| 6,280,952 B1 | | 8/2001 | Weisburg et al. |
| 6,355,421 B1 | | 3/2002 | Coull et al. |
| 6,361,945 B1 | | 3/2002 | Becker et al. |
| 6,399,302 B1 | | 6/2002 | Lannigan et al. |
| 6,451,588 B1 | | 9/2002 | Egholm et al. |
| RE37,891 E | | 10/2002 | Collins et al. |
| 6,472,522 B1 | | 10/2002 | Horn et al. |
| 6,489,464 B1 | | 12/2002 | Agrawal et al. |
| 6,528,267 B1 | | 3/2003 | Coull et al. |
| 6,534,273 B2 | | 3/2003 | Weisburg et al. |
| 6,534,274 B2 | | 3/2003 | Becker et al. |
| 6,566,055 B1 | | 5/2003 | Monforte et al. |
| 6,576,419 B1 | | 6/2003 | Wei et al. |
| 6,835,542 B2 | | 12/2004 | Becker et al. |
| 6,849,412 B2 | | 2/2005 | Becker et al. |
| 6,903,206 B1 | | 6/2005 | Becker et al. |
| 7,220,544 B2 | | 5/2007 | Inose |
| 7,230,092 B2 | | 6/2007 | Bortolin et al. |
| RE41,365 E | | 6/2010 | Bowdish et al. |
| 7,851,150 B2 | | 12/2010 | Dahlberg et al. |
| 2002/0114784 A1 | | 8/2002 | Li et al. |
| 2003/0049673 A1 | | 3/2003 | Atkinson et al. |
| 2003/0054376 A1 | * | 3/2003 | Mullis et al. ....................... 435/6 |
| 2003/0113781 A1 | | 6/2003 | Bortolin et al. |
| 2003/0194723 A1 | * | 10/2003 | Cunningham et al. ............ 435/6 |
| 2005/0186591 A1 | | 8/2005 | Bumcrot et al. |
| 2006/0057564 A1 | | 3/2006 | Wang |
| 2006/0068417 A1 | | 3/2006 | Becker et al. |
| 2006/0099619 A1 | | 5/2006 | Remacle et al. |
| 2006/0292616 A1 | | 12/2006 | Neely et al. |

FOREIGN PATENT DOCUMENTS

| | | |
|---|---|---|
| EP | 0 601 889 A2 | 6/1994 |
| EP | 1 288 313 A2 | 3/2003 |
| WO | 92/15708 A1 | 9/1992 |
| WO | 97/08183 A1 | 3/1997 |
| WO | 97/23647 A1 | 7/1997 |
| WO | 98/02582 A2 | 1/1998 |
| WO | 9850583 A2 | 11/1998 |
| WO | 99/22018 A2 | 5/1999 |
| WO | 00/01850 A2 | 1/2000 |
| WO | 00/71740 A1 | 11/2000 |
| WO | 01/94625 A2 | 12/2001 |
| WO | 02/06531 A2 | 1/2002 |
| WO | 2004/081520 A2 | 9/2004 |
| WO | 2006/007567 A2 | 1/2006 |

OTHER PUBLICATIONS

International Preliminary Report on Patentability for PCT/US2005/023555 dated Jan. 9, 2007.
Examiner's Report received in EP Patent Application 05 767 727.0 dated Jun. 22, 2007.
EP Office Action Communication in corresponding EP Patent Application EP05 767 727 dated Jun. 22, 2007.
EP Office Action Communication in corresponding EP Patent Application EP05 767 727 dated Oct. 9, 2008.
Examiner's Report received in EP Patent Application 05 767 727.0 dated Oct. 9, 2008.
Examiner's Report received in AU Patent Application 2005262357 dated Jun. 9, 2009.
AU Notice of Acceptance in corresponding AU Patent Application 2005262357 dated Oct. 19, 2009.
EP Notice of Allowance in corresponding EP Patent Application EP05 767 727 dated Nov. 11, 2009.
EP Decision to Grant Pursuant to Article 97(1) in corresponding EP Patent Application EP05 767 727 dated Apr. 1, 2010.
Armitage et al., "Hairpin-Forming Peptide Nucleic Acid Oligomers", 1998, Biochem., 37:9417-9425, USA.
Azhayeva et al., "Selective binding of looped oligonucleotides to a single-stranded DNA and its influence on replication in vitro", 1995, Nucl. Acids Res., 23(21):4255-4261, Oxford University Press, GB.
Bagwell et al., "A new homogeneous assay system for specific nucleic acid sequences: poly-dA and poly-A detection", 1994, Nucl. Acids Res., 22(12)2424-2425, Oxford University Press, GB.
Blok et al., "Amplifiable hybridization probes containing a molecular switch", 1997, Mol. Cell. Probes, 11:187-194, Academic Press Limited, USA.
Bonnet et al., "Thermodynamic Basis of the Enhanced Specificity of Structured DNA Probes", 1999, Proc. Natl Acad. Sci., 96:6171-6176, National Academy of Sciences, USA.
Bonnet et al., "Kinetics of Conformational Fluctuations in DNA Hairpin-Loops", Proc. Natl. Acad. Sci., Jul. 1998, pp. 8602-8606, vol. 95, No. 15, The National Academy of Sciences, USA.
Cardullo et al., "Detection of nucleic acid hybridization by nonradiative fluorescence resonance energy transfer", Proc. Natl. Acad. Sci., Dec. 1988, pp. 8790-8794, vol. 85, No. 23, The National Academy of Sciences, USA.
Case et al., "The unusual stability of the IS10 anti-sense RNA is critical for its function and is determined by the structure of its stem-domain", 1989, EMBO J, 8(13):4297-4305, IRL Press, Germany.
Giesendorf et al., "Molecular Beacons: A New Approach for Semiautomated Mutation Analysis", Clinical Chemistry, Mar. 1998, pp. 482-486, vol. 44, No. 3, American Association for Clinical Chemistry, Inc., USA.
Kostrikis et al., "Spectral Genotyping of Human Alleles", Science, Feb. 1998, pp. 1228-1229, vol. 279, No. 5354, American Association for the Advancement of Science, USA.
Kramer et al., "Replicatable RNA Reporter", Nature, Jun. 1989, pp. 401-402, vol. 339, No. 6223, Macmillan Magazines Ltd., GB.
Lee et al., "Allelic discrimination by nick-translation PCR with fluorogenic probes", Nucleic Acids Research, Aug. 1993, pp. 3761-3766, vol. 21, No. 16, Oxford University Press, GB.
Leone et al., "Molecular beacon probes combined with amplification by NASBA enable homogeneous, real-time detection of RNA", Nucleic Acids Research, May 1998, pp. 2150-2155, vol. 26 No. 9, Oxford University Press, GB.
Livak et al., "Oligonucleotides with Fluorescent Dyes at Opposite Ends Provide a Quenched Probe System Useful for Detecting PCR Product and Nucleic Acid Hybridization", PCR Methods and Applications, Jun. 1995, pp. 357-362, vol. 4, No. 6, Cold Spring Harbor Laboratory Press, USA.
Lubini et al., "Stabilizing effects of the RNA 2'-substituent: crystal structure of an oligodeoxynucleotide duplex containing 2'-O-methylated adenosines", 1994, Chem. & Biol., 1:39-45, Cell Press, USA.
Marras et al., "Multiplex Detection of Single-Nucleotide Variations Using Molecular Beacons", 1999, Genetic Analysis Biomolecular Engineering, 14:151-156, Elsevier Trends Journal, Cambridge, GB.
Mergny et al., "Fluorescence energy transfer as a probe for nucleic acid structures and sequences", Nucleic Acids Research, Mar. 1994, pp. 920-928, vol. 22, No. 6, Oxford University Press, GB.
Morrison et al., "Solution-Phase Detection of Polynucleotides Using Interacting Fluorescent Labels and Competitive Hybridization", Analytical Biochemistry, Dec. 1989, pp. 231-244, vol. 183, No. 2, Academic Press, Inc., USA.
Morrison et al., "Sensitive Fluorescence-Based Thermodynamic and Kinetic Measurements of DNA Hybridization in Solution", Biochemistry, Mar. 1993, pp. 3095-3104, vol. 32, No. 12, American Chemical Society, USA.
Ortiz et al., "PNA molecular beacons for rapid detection of PCR amplicons", Molecular and Cellular Probes, Aug. 1998, pp. 219-226, vol. 12, No. 4, Academic Press, GB.
Piatek et al., "Molecular beacon sequence analysis for detecting drug resistance in *Mycobacterium tuberculosis*", Nature Biotechnology, Apr. 1998, pp. 359-363, vol. 16, No. 4, Nature Publishing Co., USA.

Refregiers et al., "Fluorescence Resonance Energy Transfer Analysis of the Degradation of an Oligonucleotide Protected by a Very Stable Hairpin", 1996, J. Biom. Struc. Dyn., 14(3):365-371, Adenine Press, USA.

Tang et al., "Self-stabilized antisense oligodeoxynucleotide phosphorothioates: properties and anti-HIV activity", 1993, Nucl. Acids Res., 21(11):2729-2735, Oxford University Press, GB.

Tyagi et al., "Molecular Beacons: Probes that Fluoresce upon Hybridization", Nature Biotechnology, Mar. 1996, pp. 303-308, vol. 14, No. 3, Nature Publishing Co., USA.

Varani, "Exceptionally Stable Nucleic Acid Hairpins", Annu. Rev. Biophys. Biomol. Struct., 1995, pp. 379-404, vol. 24, Annual Reviews Inc., USA.

Examiner's Report received in JP Patent Application 2007-520409.

Notice of Allowance and allowed claims, Japanese Application No. 2007-520409, mailed May 14, 2012.

USPTO Office Action, U.S. Appl. No. 13/087,282, mailed Aug. 1, 2012.

Bonaldo et al., "Normalization and Subtraction: Two Approaches to Facilitate Gene Discovery." Genome Res., 1996, pp. 791-806, vol. 6 (9), Cold Water Spring Laboratory Press, Cold Spring Harbor, NY.

Chen et al., "Real-time quantification of microRNAs by stem-loop RT-PCR." Nucleic Acids Research, 2005, vol. 33 (20), Oxford University Press, Oxford, UK.

Raymond et al., "Simple, quantitative primer-extension PCR assay for direct monitoring of microRNAs and short-interfering RNAs," RNA Society, 2005, pp. 1737-1744, vol. 11(11), Cold Spring Harbor Laboratory Press, Cold Spring Harbor, NY.

Office Action in corresponding U.S. Appl. No. 11/173,915 dated Mar. 23, 2007.

Office Action in corresponding U.S. Appl. No. 11/173,915 dated Oct. 22, 2007.

Office Action in corresponding U.S. Appl. No. 11/173,915 dated May 14, 2008.

Office Action in corresponding U.S. Appl. No. 11/173,915 dated Nov. 14, 2008.

Office Action in corresponding U.S. Appl. No. 11/173,915 dated Jun. 12, 2009.

Office Action in corresponding U.S. Appl. No. 11/173,915 dated Dec. 18, 2009.

Examiner Interview in corresponding U.S. Appl. No. 11/173,915 dated Mar. 4, 2010.

Office Action in corresponding U.S. Appl. No. 11/173,915 dated Apr. 16, 2010.

Office Action in corresponding U.S. Appl. No. 11/173,915 dated Jul. 8, 2010.

Advisory Action in corresponding U.S. Appl. No. 11/173,915 dated Jul. 8, 2010.

Pre-Brief Appeal Conference Decision in corresponding U.S. Appl. No. 11/173,915 dated Sep. 2, 2010.

Office Action in corresponding U.S. Appl. No. 11/173,915 dated Mar. 18, 2011.

Examiner Interview in corresponding U.S. Appl. No. 11/173,915 dated Mar. 18, 2011.

International Preliminary Report in corresponding International Application PCT/US2005/023555 dated Jan. 18, 2007.

AU 1st Exam Report in corresponding AU Application 2005-262357 dated Jun. 9, 2009.

AU Notice of Acceptance in corresponding AU Application 2005-262357 dated Oct. 19, 2009.

EP Communication Pursuant to Article 96(2) in corresponding EP Application 05 767 727.0 dated Jun. 22, 2007.

EP Communication Pursuant to Article 94(3) in corresponding EP Application 05 767 727.0 dated Oct. 9, 2008.

EP Communication Pursuant to Rule 71(3) in corresponding EP Application 05 767 727.0 dated Nov. 11, 2009.

EP Decision to Grant Pursuant to Rule 97(1) in corresponding EP Application 05 767 727.0 dated Apr. 1, 2010.

Notice of Allowance, Canadian Patent Application No. 2,572,472, mailed Dec. 4, 2012.

* cited by examiner

SEQUENCE LISTING

<160> NUMBER OF SEQ ID NOS: 7

<210> SEQ ID NO 1
<211> LENGTH: 47
<212> TYPE: DNA
<213> ORGANISM: Artificial
<220> FEATURE:
<223> OTHER INFORMATION: hairpin capture probe oligonucleotide
<220> FEATURE:
<221> NAME/KEY: misc_feature
<222> LOCATION: (1)..(12)
<223> OTHER INFORMATION: poly-T region that hybridizes to the 3' poly-A
      region to form the double-stranded portion of the hairpin
      oligonucleotide
<220> FEATURE:
<221> NAME/KEY: misc_feature
<222> LOCATION: (13)..(35)
<223> OTHER INFORMATION: model target-complementary region that forms a
      loop in the hairpin capture probe oligonucleotide
<220> FEATURE:
<221> NAME/KEY: misc_feature
<222> LOCATION: (36)..(47)
<223> OTHER INFORMATION: poly-A region that hybridizes to 5' poly-T
      region to form the double-stranded portion of the hairpin
      oligonucleotide

<400> SEQUENCE: 1
tttttttttt ttnnnnnnnn nnnnnnnnnn nnnnaaaaa aaaaaaa                      47

<210> SEQ ID NO 2
<211> LENGTH: 47
<212> TYPE: DNA
<213> ORGANISM: Artificial
<220> FEATURE:
<223> OTHER INFORMATION: hairpin capture probe oligonucleotide
<220> FEATURE:
<221> NAME/KEY: misc_feature
<222> LOCATION: (1)..(12)
<223> OTHER INFORMATION: 5' region that hybridizes to the 3' poly-A
      region to form a substantially double-stranded portion of the
      hairpin oligonucleotide
<220> FEATURE:
<221> NAME/KEY: misc_feature
<222> LOCATION: (13)..(35)
<223> OTHER INFORMATION: model target-complementary region that forms
      the loop in the hairpin capture probe  oligonucleotide
<220> FEATURE:
<221> NAME/KEY: misc_feature
<222> LOCATION: (36)..(47)
<223> OTHER INFORMATION: 3' poly-A region that hybridizes to the 5'
      region to form a substantially double-stranded portion of the
      hairpin oliogonucleotide

<400> SEQUENCE: 2
tttttatttt ttnnnnnnnn nnnnnnnnnn nnnnnaaaaa aaaaaaa                     47

<210> SEQ ID NO 3
<211> LENGTH: 39
<212> TYPE: DNA
<213> ORGANISM: Artificial
<220> FEATURE:
<223> OTHER INFORMATION: linear capture probe oligonucleotide
<220> FEATURE:
<221> NAME/KEY: misc_feature
<222> LOCATION: (1)..(24)
<223> OTHER INFORMATION: model target-complementary region that includes
      the same model target-complementary regions of SEQ ID NOs 1 and 2
<220> FEATURE:
<221> NAME/KEY: misc_feature
<222> LOCATION: (25)..(39)
<223> OTHER INFORMATION: capture portion of the linear capture probe

<400> SEQUENCE: 3
nnnnnnnnnn nnnnnnnnnn nnnntttaaa aaaaaaaaa                                    39

<210> SEQ ID NO 4
<211> LENGTH: 36
<212> TYPE: DNA
<213> ORGANISM: Artificial
<220> FEATURE:
<223> OTHER INFORMATION: poly-T containing oligonucleotide strand of a
      partially or completely double-stranded capture probe when
      hybridized with SEQ ID NO:5 or SEQ ID NO:6
<220> FEATURE:
<221> NAME/KEY: misc_feature
<222> LOCATION: (1)..(15)
<223> OTHER INFORMATION: poly-T region that hybridizes to the 3' poly-A
      region of SEQ ID NO:5 or SEQ ID NO:6
<220> FEATURE:
<221> NAME/KEY: misc_feature
<222> LOCATION: (16)..(36)
<223> OTHER INFORMATION: target-complementary region

<400> SEQUENCE: 4 ttttttttttt tttttagagg atgggttttc tagggg                                      36

<210> SEQ ID NO 5
<211> LENGTH: 35
<212> TYPE: DNA
<213> ORGANISM: Artificial
<220> FEATURE:
<223> OTHER INFORMATION: poly-A containing strand that forms a partially
      double-stranded capture probe when hybridized with SEQ ID NO:4
<220> FEATURE:
<221> NAME/KEY: misc_feature
<222> LOCATION: (21)..(35)
<223> OTHER INFORMATION: poly-A region that hybridizes to the poly-T
      region of SEQ ID NO:4

<400> SEQUENCE: 5
ctctctctct ctctctctct aaaaaaaaaa aaaaa                                        35

<210> SEQ ID NO 6
<211> LENGTH: 36
<212> TYPE: DNA
<213> ORGANISM: Artificial
<220> FEATURE:
<223> OTHER INFORMATION: poly-A containing oligonucleotide that forms a
      double-stranded capture probe when hybridized with SEQ ID NO:4
<220> FEATURE:
<221> NAME/KEY: misc_feature
<222> LOCATION: (1)..(21)
<223> OTHER INFORMATION: sequence complementary to the target-
      complementary region of SEQ ID NO:4
<220> FEATURE:
<221> NAME/KEY: misc_feature
<222> LOCATION: (22)..(36)
<223> OTHER INFORMATION: poly-A region that hybridizes to the poly-T
      region of SEQ ID NO:4

<400> SEQUENCE: 6
cccctagaaa acccatcctc taaaaaaaaa aaaaaa                                       36

<210> SEQ ID NO 7
<211> LENGTH: 20
<212> TYPE: DNA
<213> ORGANISM: Artificial
<220> FEATURE:
<223> OTHER INFORMATION: detection probe oligonucleotide

```
<400> SEQUENCE: 7
gtcagataac tgtccatgac                                                    20
```

METHODS AND COMPOSITIONS TO DETECT NUCLEIC ACIDS IN A BIOLOGICAL SAMPLE

RELATED APPLICATION

This application is a divisional application of U.S. application Ser. No. 11/173,915, filed Jun. 29, 2005 and claims priority to provisional application No. 60/585,421, filed Jul. 1, 2004, both of which are incorporated by reference herein.

FIELD OF THE INVENTION

The invention is related to the field of nucleic acid assays, and particularly to detection of a specific target nucleic acid present in a sample, such as a small RNA or DNA sequence present in a biological sample.

BACKGROUND

Detection of nucleic acids in a sample is useful in diagnostic, therapeutic, forensic, agricultural, food science applications and other areas. Methods of nucleic acid detection include those that use physical separation and detection of a nucleic acid, such as by capturing the nucleic acid in or on a matrix or support and detecting the captured nucleic acids by using a means to visualize the nucleic acid, such as a dye or intercalating agent, or by hybridizing a detectable probe to the nucleic acid. Known methods for separating and detecting nucleic acids use electrophoretic separation of nucleic acids by size, e.g. by using a gel or other chromatographic matrix, followed by staining or attaching a probe to the separated nucleic acids to produce a signal to indicate the presence of the nucleic acid in the sample. Some methods indirectly detect nucleic acids by producing a product made from using a target nucleic acid as a template and detecting the product, e.g., detecting an RNA transcript made from a DNA, or a translated protein made from an RNA transcript. Other indirect methods detect a product made by an enzymatic reaction associated with the nucleic acid to be detected, e.g., an enzyme-linked probe hybridized to the target nucleic acid which produces a detectable response when the enzyme's substrate is provided. Some methods of nucleic acid detection rely on amplifying a nucleic acid sequence to produce a larger quantity of nucleic acid that is detected. Examples of amplification methods include producing many copies of a cloned sequence and in vitro amplification procedures that use enzymatic synthesis of multiple copies of a nucleic acid sequence.

Many of the techniques for detecting nucleic acids require the presence of a relatively large amount or proportion of the target nucleic acid in the sample, while other techniques use nucleic acid amplification to increase the amount or proportion of the nucleic acid to be detected from a smaller amount of the target nucleic acid in a sample. Enrichment of some or all of the nucleic acid present in a sample may facilitate detection of the nucleic acid of interest. Many known procedures for nucleic acid enrichment and detection are laborious, time-consuming, or require use of equipment or hazardous chemicals (e.g., chaotropes, mutagens, or radioactive compounds) that make such procedures undesirable for many applications, such as for rapid screening of many samples, point-of-care diagnostics, or detection at a site outside of a laboratory. Thus, there remains a need for a method that provides relatively simple procedures and sufficient sensitivity and/or specificity to detect a nucleic acid of interest.

The physical nature or relative abundance of some nucleic acids may impede their detection in a sample. For example, small RNA (about 17-27 nt), such as microRNA (miRNA), small or short interfering RNA (siRNA), short hairpin RNA (shRNA), and small nuclear RNA (snRNA) are difficult to separate from other sample components and/or to detect by using known methods. Small RNA are often relatively rare in a biological sample which contributes to the difficulty of their detection. Because small RNA are important regulatory molecules that modulate or silence gene expression via RNA interference (RNAi), they may be important disease preventive or therapeutic agents. Thus, there is a need for a method that rapidly detects the presence of small RNA in biological samples to determine their presence, stability, therapeutic efficacy, or other characteristics in a biological sample without requiring extensive processing or nucleic acid amplification. There is a further need to detect localized small RNA in a variety of biological samples to avoid conditions that lead to inadvertent suppression of non-targeted gene functions by small RNA. Current methods for detecting small RNA or their effects in biological samples are time consuming and laborious, e.g., in situ hybridization, nuclease protection assays, Northern blots to detect RNA, Western blots to detect proteins, immunoassays, and fluorescence detection assays (PCT App. Nos. WO 0044914, Li et al., WO 05004794, Bumcrot et al.).

This application responds to the need for efficient nucleic acid detection assays by disclosing methods and compositions useful for the rapid detection of nucleic acids in samples, including small RNA in biological samples.

SUMMARY OF THE INVENTION

An aspect of the invention is a method of detecting the presence of a nucleic acid present in a sample which includes the steps of: providing a sample containing a target nucleic acid, mixing the sample with a nucleic acid capture probe that forms under hybridizing conditions a partially double-stranded hairpin structure made up of an internal target-complementary sequence, flanked by a capture region, and a terminal region that binds to the capture region to form a double-stranded stem portion of the hairpin structure in which the target-complementary region forms a substantially single-stranded loop portion, specifically hybridizing the target-complementary sequence of the capture probe to a target sequence in the target nucleic acid, binding the capture region to an immobilized probe attached to a capture support by binding together members of a specific binding pair, thereby forming a capture hybrid made up of the target nucleic acid, the capture probe, and the immobilized probe attached to the capture support, separating the capture hybrid attached to the capture support from sample components, releasing the target nucleic acid from the capture hybrid, then specifically hybridizing a detection probe to the target nucleic to form a detection hybrid, and detecting a signal produced from the detection hybrid to indicate the presence of the target nucleic acid in the sample. In one embodiment, the capture region is located near the 3' end of the capture probe and the terminal region is located near the 5' end of the capture probe. In another embodiment, the capture region is located near the 5' end of the capture probe and the terminal region is located near the 3' end of the capture probe. In one embodiment, the step of binding the capture region to the immobilized probe hybridizes complementary sequences of the capture region and the immobilized probe. In another embodiment, binding the capture region to the immobilized probe binds together non-nucleic acid members of a specific binding pair, such as a ligand and its receptor. In one embodiment, releasing the target nucleic acid from the capture hybrid further releases the capture probe from the immobilized probe. In one embodiment, the detecting step uses a detection probe that hybridizes specifically to a target sequence that is the same target sequence that hybridizes to the target-complementary sequence of the capture probe. In another embodiment, the detection probe hybridizes specifically to a target sequence that differs from or overlaps the target sequence that hybridizes to the target-complementary sequence of the capture probe. In a preferred embodiment, the detecting step detects a signal is produced in a homogeneous reaction.

Another aspect of the invention is a method of detecting the presence of a target nucleic acid present in a sample that includes the steps of: providing a sample containing a target nucleic acid, mixing the sample with a capture probe that is at least a partially double-stranded structure made up of a first strand and a second strand of nucleic acid, wherein the first strand includes a target-complementary region and a capture region, and the second strand contains a sequence complementary to a sequence of the first strand, specifically hybridizing the target-complementary region of the capture probe to a target sequence in the target nucleic acid, binding the capture region to an immobilized probe attached to a capture support, thereby forming a capture hybrid made up of the target nucleic acid, the first strand of the capture probe, and the immobilized probe attached to the capture support, separating the capture hybrid attached to the capture support from other sample components, releasing the target nucleic acid from the capture hybrid, then specifically hybridizing a detection probe to the target nucleic acid to form a detection hybrid, and detecting a signal produced from the detection hybrid, thereby indicating the presence of the target nucleic acid in the sample. In one embodiment, the first strand contains a 5' capture region covalently linked to a 3' target-complementary region, and the second strand contains a 3' sequence complementary to the capture region of the first strand, thereby forming a partially double-stranded structure when the capture region of the first strand hybridizes to the complementary 3' sequence of the second strand. In another embodiment, the first strand contains a 5' target-complementary region covalently linked to a 3' capture region, and the second strand contains a 5' sequence complementary to the 3' capture region of the first strand, thereby forming a partially double-stranded structure when the capture region of the first strand hybridizes to the complementary 5' sequence of the second strand.

Another aspect of the invention is a nucleic acid capture probe that forms at least a partially double-stranded structure under hybridizing conditions and includes a target-complementary sequence and a capture region that binds to an immobilized probe by using members of a specific binding pair. In one embodiment, the partially double-stranded structure is a hairpin structure made up of a contiguous linear sequence that includes an internal target-complementary sequence, flanked by the capture region and a terminal region that binds to the capture region to form a double-stranded stem portion of the hairpin structure and the target-complementary region forms a substantially single-stranded loop portion of the hairpin structure. It will be appreciated that the capture region may be a 5' region and the terminal region is a 3' region of the contiguous linear sequence, or alternatively, the capture region may be a 5' region and the terminal region is a 3' region of the contiguous linear sequence that forms a hairpin structure. In another capture probe embodiment, the structure is made of up of a first strand that includes the target-complementary region and the capture region, and a separate second strand that includes a sequence complementary to a sequence of the first strand such that hybridization of the complementary sequences of the first strand and second strand produce at least a partially double-stranded structure. It will be appreciated that the first strand may have a 5' target-complementary region and a 3' capture region, or alternatively, a 3' target-complementary region and a 5' capture region, and that the complementary sequence of the separate second strand may be complementary to either the target-complementary region or the capture region of the first strand. In a preferred embodiment, the complementary sequence of the second strand is complementary to the capture region of the first strand. Another embodiment is a kit that includes the capture probe that forms a partially double-stranded hairpin structure and a detection probe that hybridizes specifically to a target nucleic acid that contains a sequence that hybridizes to the target-complementary sequence of the hairpin structure capture probe. In one embodiment of the kit, the detection probe hybridizes specifically to the same target nucleic acid sequence that hybridizes to the target-complementary sequence of the capture probe. In another embodiment, the kit further includes an immobilized probe attached to a capture support, in which the immobilized probe includes a member of a specific binding pair that binds specifically to the capture probe. In one kit, the specific binding pair members are complementary sequences that hybridize the capture probe to the immobilized probe under hybridizing conditions. Another kit embodiment includes the capture probe made of up of a first strand that includes the target-complementary region and the capture region and a separate second strand that includes a sequence complementary to a sequence of the first strand, and a detection probe that hybridizes specifically to a target nucleic acid that contains a sequence that hybridizes to the target-complementary sequence of that capture probe.

DETAILED DESCRIPTION

Figure 1:
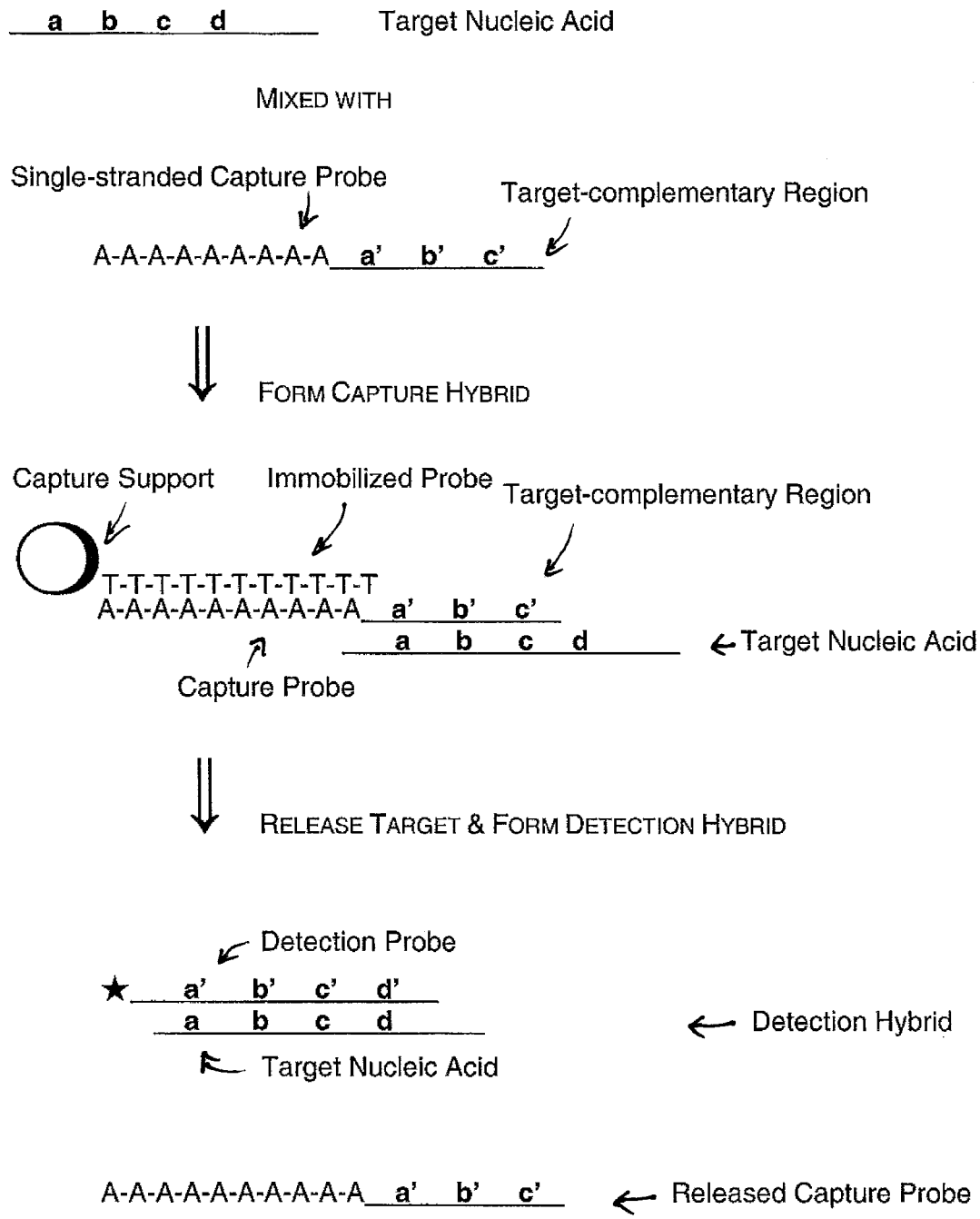
FIG. 1 illustrates an embodiment showing capture and detection of a target nucleic acid by mixing a target nucleic acid (shown as the sequence a b c d) with a single-stranded capture probe to form a capture hybrid made up of the target nucleic acid hybridized to target-complementary region (shown as the sequence a' b' c') of the capture probe and an immobilized probe (shown as poly-T attached to a capture support) hybridized to another portion of the capture probe (shown as poly-A), followed by release of the target nucleic acid and formation of a detection hybrid made up of a detection probe (shown as the sequence a' b' c' d') hybridized to the target nucleic acid, where the detection hybrid produces a detectable signal (shown by the black star icon) to indicate the presence of the target.

This invention is useful for detection of a target nucleic acid of interest present in a sample. The methods use relatively few and easily performed steps to isolate and/or concentrate the target nucleic acid from other sample components and to detect the target nucleic acid. The methods include a capture step in which the target nucleic acid is captured by using one or more capture probes to form of a capture hybrid that is linked to a capture support, which together are separated from other sample components. Then, the target nucleic acid in the capture hybrid is released from the capture support and the target nucleic acid is detected by using a detection probe to form a detection hybrid that causes production of a detectable signal. Although any specific binding pair may be used to link the components of the capture hybrid and the detection hybrid, preferred embodiments use nucleic acid hybridization to form the capture and detection hybrids. In a preferred embodiment, the detection step is performed in a homogeneous reaction assay in which unbound detection probe does not interfere with detection of a signal resulting from the bound detection probe in the detection hybrid. This contributes to the simplicity and efficiency of the system because unattached detection probe does not have to be removed from the mixture before detection of the signal from the detection hybrid.

These methods are useful particularly for detecting small target nucleic acids that may be present at dilute concentrations in a sample, e.g., small nucleic acids excreted in urine or present in a cellular or tissue extract. These methods are also useful for assaying many samples, preferably simultaneously or in rapid succession, such as in an automated high throughput system because the capture and detection steps can be performed in a single reaction chamber per sample.

To better understand the various embodiments of the invention, some of the terms used in the description of the invention are more fully described below.

By "nucleic acid" is meant a polydeoxyribonucleotide (DNA or an analog thereof) or polyribonucleotide (RNA or an analog thereof) made up of at least two, and preferably ten or more bases linked by a backbone structure. In DNA, the common bases are adenine (A), guanine (G), thymine (T) and cytosine (C), whereas in RNA, the common bases are A, G, C and uracil (U, in place of T), although nucleic acids may include base analogs (e.g., inosine) and abasic positions (i.e., a phosphodiester backbone that lacks a nucleotide at one or more positions, U.S. Pat. No. 5,585,481). Nucleic acids include polynucleotides or polymers and oligonucleotides or oligomers of DNA and RNA, which may be single-stranded (ss), double-stranded (ds), or triple-stranded. Oligomers generally refer to nucleic acids that comprise 1,000 or fewer nucleotides, and often comprise two to about 100 nucleotides, whereas polymers generally refer to nucleic acids that comprise 1,000 or more nucleotides, including nucleic acid structures comprised of many thousands of nucleotides, such as plasmids, cosmids, genes, chromosomes, genomes and the like which are well known in the art. Also included in the term are "locked nucleic acids" (LNA), a nucleic acid analogue that contains one or more LNA nucleotide monomers with a bicyclic furanose unit locked in an RNA mimicking sugar conformation, to enhance hybridization affinity toward complementary ssRNA, or complementary ssDNA or dsDNA (Vester B. and Wengel J., 2004, Biochemistry. 43(42):13233-41).

A nucleic acid "backbone" refers to groups or linkages known in the art (Eschenmoser, 1999, Science 284:2118-2124), such as, e.g., sugar-phosphodiester linkages, 2'-O-methyl linkages, guanidine linkers in DNA ("DNG"), S-methylthiourea linkers, methylphosphonate linkages, phosphoramidite linkages, amide backbone modifications as in polyamide or peptide nucleic acids (PNA), phosphorothioate linkages, phosphonic ester nucleic acid linkages, pyranosyl oligonucleotide linkages, bicyclo- and tricyclo-nucleic acid linkages, formacetal and 3'-thioformacetal linkages, morpholino linkages, or other modifications of the natural phosphodiester internucleoside bond, or combinations of such linkages in a single backbone (Majlessi et al., 1998, Nucl. Acids Res. 26(9):2224-2229; Dempcy et al., 1995, Proc. Natl. Acad. Sci. USA 92:6097-6101; Browne et al., 1995, Proc. Natl. Acad. Sci. USA 92:7051-7055; Arya & Bruice, 1998, J. Am. Chem. Soc. 120:6619-6620; Reynolds et al., 1996, Nucl. Acids Res. 24(22):4584-4591; Gryaznov & Chen, 1994, Am. Chem. Soc. 116:3143-3144; Chaturvedi at al., 1996, Nucl. Acids Res. 24(12):2318-2323; Hyrup & Nielsen, 1996, Bioorg. & Med. Chem. 4:5-23; Hydig-Hielsen et al., PCT App. No. WO 95/32305; Mesmaeker et al., Syn. Lett., November 1997:1287-1290; Peyman et al., 1996, Angew. Chem. Int. Ed. Engl. 35(22):2636-2638; Aerschot et al., 1995, Angew. Chem. Int. Ed. Engl. 34(12):1338-1339; Koshkin et al., 1998, J. Am. Chem. Soc. 120:13252-13253; Steffens & Leumann, 1997, J. Am. Chem. Soc. 119:11548-11549; Jones et al., 1993, J. Org. Chem. 58:2983-2991; Summerton & Weller, 1997, Antisense & Nucl. Acid Drug Dev. 7:187-195; Stirchak et al., 1989, Nucl. Acids Res. 17(15): 6129-6141). A nucleic acid backbone may include a mixture of linkages in the same nucleic acid (e.g., sugar-phosphodiester and 2'-O-methyl linkages) or may have all of one type of linkages (e.g., all 2'-O-methyl or all amide modification linkages in an oligomer).

A "target" or "target sequence" or "target nucleic acid" refers to a sequence of nucleotide bases present in a nucleic acid, or portion of a nucleic acid, to which another sequence binds, e.g., by using standard complementary base pairing. For example, the target sequence may be a relatively small part of a larger nucleic acid, such as a specific subsequence contained in a gene or messenger RNA (mRNA). Those skilled in the art will appreciate that a target nucleic acid may exist in different forms, i.e., single-stranded, double-stranded, triple-stranded, or mixtures thereof, such as in a partially double-stranded hairpin structure or partially double-stranded duplex structure, and will further appreciate that a target sequence may be present on any strand (+ or −) of the structure. For simplicity, a target nucleic acid may be described as all or part of a single strand, but this is not meant to limit the meaning of a target to one or a particular nucleic acid strand. It is well known in the art that a multi-stranded nucleic acid is readily converted to its single-strand components by using standard methods, such as by heating a nucleic acid above its melting temperature (Tm) and/or by using chemical denaturants.

By "complementary" or "complementarity of" nucleic acids is meant that a nucleotide sequence in one strand of nucleic acid, due to orientation of the functional groups, will hydrogen bond to another sequence on an opposing nucleic acid strand. The complementary bases typically are, in DNA, A with T and, C with G, and, in RNA, C with G, and U with A. "Substantially complementary" means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations known to those skilled in the art to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41 (% G+C), although other Tm computations are known in the art which take into account nucleic acid structural characteristics.

"Hybridization condition" refers to the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other well known factors, such as the length of incubation time or reaction chamber dimensions may contribute to the environment (e.g., Sambrook at al., *Molecular Cloning, A Laboratory Manual*, 2$^{nd}$ ed., pp. 1.90-1.91, 9.47-9.51, 11.47-11.57 (Cold Spring Harbor Laboratory Press, Cold Spring Harbor, N.Y., 1989)).

A "label" refers to a molecular moiety that is detectable or produces a detectable response or signal directly or indirectly, e.g., by catalyzing a reaction that produces a detectable signal. Labels include luminescent moieties (such as fluorescent, bioluminescent, or chemiluminescent compounds), radioisotopes, members of specific binding pairs (e.g., biotin and avidin), enzyme or enzyme substrate, reactive groups, or chromophores, such as a dye or particle that results in detectable color.

A "detection probe" is an oligomer or polymer that binds specifically to a target sequence and which binding results, directly or indirectly, in a detectable signal to indicate the presence of the target sequence. A detection probe need not be labeled to produce a detectable signal, e.g., an electrical impulse resulting from binding the probe to its target sequence may be the detectable signal. A "labeled probe" is a probe that contains or is linked, directly or indirectly, to a label. Methods of making and/or using labeled probes are well known in the art (e.g., Sambrook et al., *Molecular Cloning, A Laboratory Manual*, 2nd ed., Chapt. 10; U.S. Pat. Nos. 6,361,945, Becker et al.; 5,658,737, Nelson et al.; 5,656,207, Woodhead et al.; 5,547,842, Hogan et al.; 5,283,174, Arnold et al.; 4,581,333, Kourilsky et al.; 5,731,148, Becker et al.). For example, detection probes may include a non-nucleotide linker and a chemiluminescent label attached to the linker (U.S. Pat. Nos. 5,185,439, 5,585,481 and 5,639,604, Arnold et al.).

"Homogeneous detectable label" refers to a label whose presence can be detected in a homogeneous manner depending on whether the label is bound or unbound to a target. A homogeneous detectable label can be detected in a "homogeneous reaction" without physically separating unbound forms of the label from the mixture before the detection step. It will be appreciated that a homogeneous reaction may occur in solution or on a support such as a microarray, biochip, or gene chip. Preferred homogeneous detectable labels and conditions for their detection have been described previously in detail (U.S. Pat. Nos. 5,283,174, Arnold et al.; 5,656,207, Woodhead et al.; 5,658,737, Nelson et al.).

An "immobilized probe" provides a means for joining a capture hybrid containing a target nucleic acid to a capture support. A preferred immobilized probe is a nucleic acid oligomer or polymer joined to a support which binds, directly or indirectly, to a target nucleic acid to facilitate separation of the bound target nucleic acid from unbound material, such as other sample components. In a preferred embodiment, the target nucleic acid is indirectly bound to the immobilized probe via a capture probe. Any of a variety of materials may be used as a capture support, e.g., matrices or particles made of nitrocellulose, nylon, glass, polyacrylate, mixed polymers, polystyrene, silane polypropylene, and magnetically attractable materials. Monodisperse magnetic spheres are a preferred embodiment of a capture support because they are relatively uniform in size and readily retrieved from solution by applying a magnetic force to the reaction container, preferably in an automated system. An immobilized probe may be linked directly to the capture support, e.g., by using any of a variety of covalent linkages, chelation, or ionic interaction, or may be linked indirectly via one or more linkers joined to the support.

A "capture probe" provides a means for joining a target nucleic acid and an immobilized probe, preferably by hybridization of complementary sequences. A capture probe includes a target-complementary region of sequence and a means for attaching the capture probe, or a hybridization complex that includes the capture probe, to an immobilized probe. Such attaching means may be a region of sequence that is complementary to a sequence of an immobilized probe, or a member of another specific binding pair (e.g., biotin and avidin or streptavidin). In a preferred embodiment, a capture probe includes is a nucleic acid homopolymer (e.g., poly-A or poly-T) that is covalently attached to the target-complementary region of the capture probe and that hybridizes under appropriate conditions to a complementary homopolymer of the immobilized probe (e.g., poly-T or poly-A, respectively) as previously described (U.S. Pat. No. 6,110,678 to Weisburg et al.).

A "sample" or "biological sample" refers to any composition or mixture in which a target nucleic acid of interest may be present, including but not limited to plant or animal materials, waste materials, materials for forensic analysis, environmental samples, and the like. A biological sample includes any tissue, cell, or extract derived from a living or dead organism which may contain a target nucleic acid, e.g., peripheral blood, bone marrow, plasma, serum, biopsy tissue including lymph nodes, respiratory tissue or exudates, gastrointestinal tissue, urine, feces, semen, or other body fluids.

"Separating" or "isolating" or "purifying" refers to removing one or more components from a complex mixture, such as a sample. Sample components may include target and non-target nucleic acids, and other materials such as salts, acids, bases, detergents, proteins, carbohydrates, lipids and other organic or inorganic materials. Preferably, a separating, isolating or purifying step removes at least 70%, preferably at least 90%, and more preferably about 95% of the target nucleic acids from other sample components. A separating, isolating or purifying step may optionally include additional washing steps to remove non-target sample components.

"Release" of a capture hybrid refers to separating one or more components of a capture hybrid from each other, such as separating a target nucleic acid from a capture probe, and/or a capture probe from an immobilized probe. Release of the target nucleic acid strand separates the target from other components of a capture hybrid and makes the target available for binding to a detection probe. Other components of the capture hybrid may remain bound, e.g., the capture probe strand to the immobilized probe on a capture support, without affecting target detection. Release of one or more capture hybrid components may be accomplished by changing one or more conditions to promote dissociation of components (e.g., heating above Tm, changing salt concentrations, adding denaturants or competitive binding moieties to the mixture), or by using other well known methods such as strand displacement.

Figure 2:
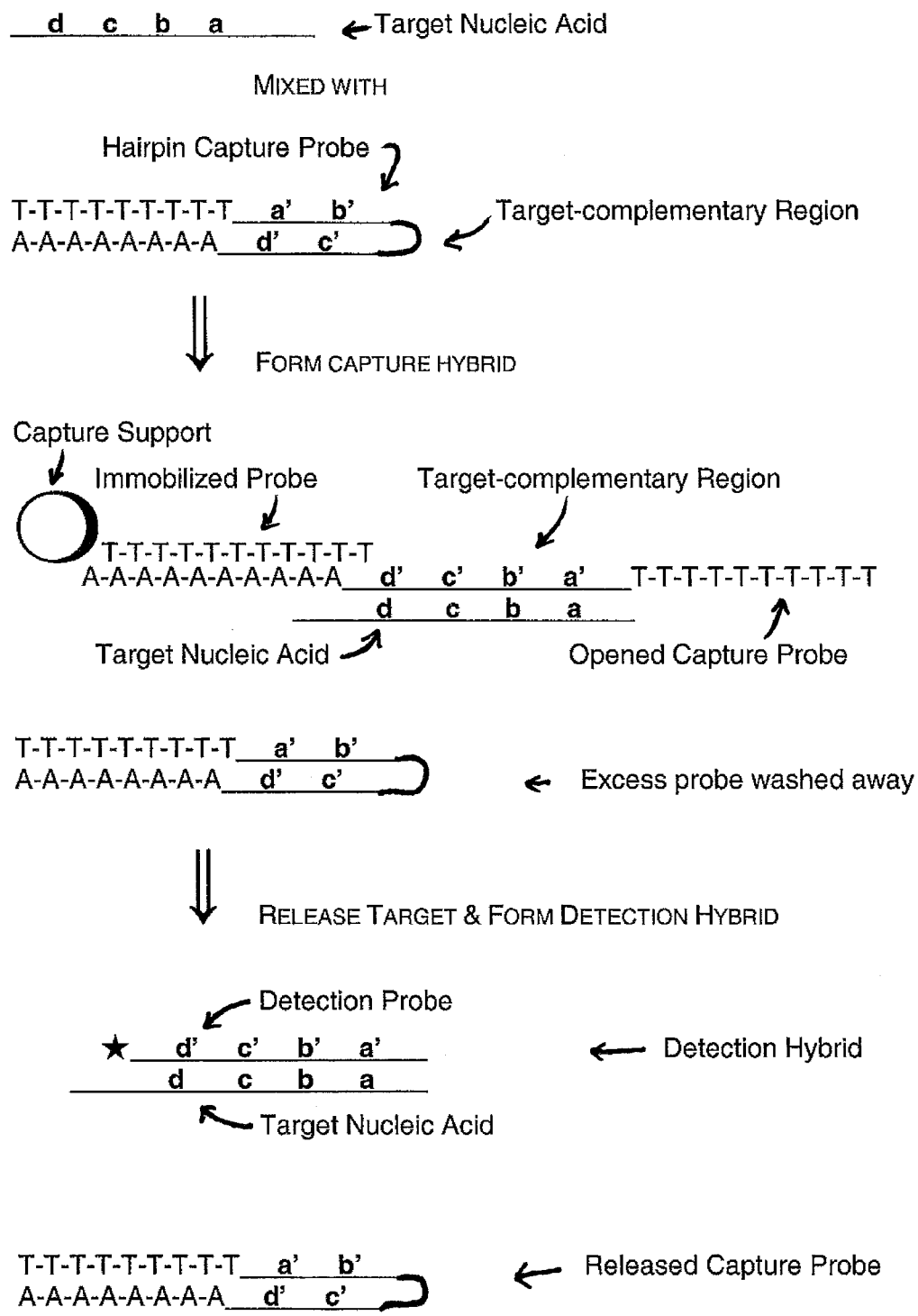
FIG. 2 illustrates an embodiment showing capture and detection of a target nucleic acid by mixing target nucleic acid (shown as the sequence d c b a) with a hairpin capture probe which has complementary sequences at its 5' and 3' ends (shown as poly-T and poly-A regions) flanking a target complementary region (shown as the sequence a' b' c' d') to form a capture hybrid made up of the target nucleic acid hybridized to target-complementary region of the opened capture probe, and a portion of a capture probe (poly-A region) hybridized to a complementary immobilized probe (shown as poly-T attached to a capture support), followed by releasing the target into solution where it forms a detection hybrid made up of a detection probe (shown by the sequence d' c' b' a') hybridized to the target nucleic acid to produce a detectable signal (shown by the black star icon) to indicate the presence of the target.
Figure 3:
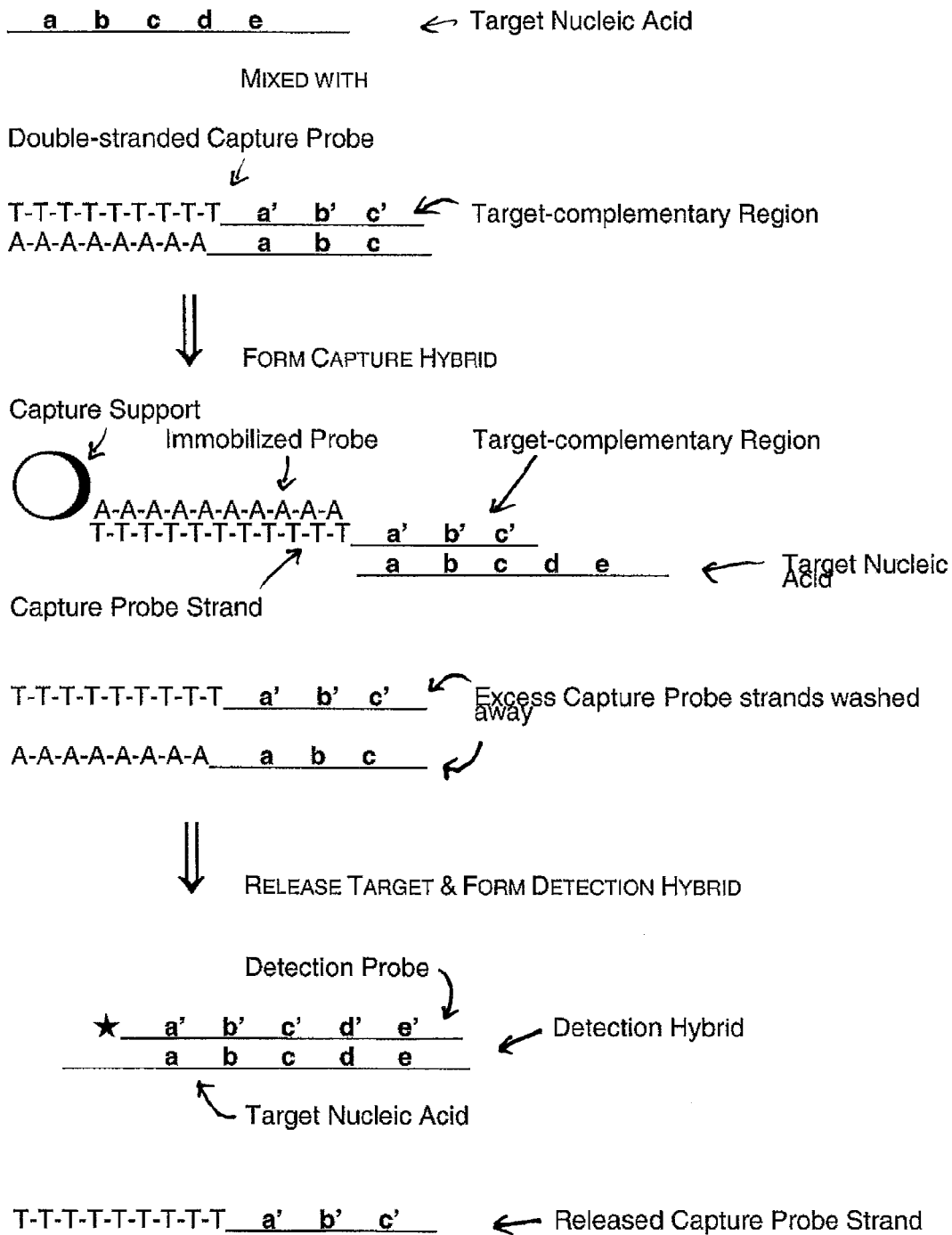
FIG. 3 illustrates an embodiment showing capture and detection of a target nucleic acid that mixes the target nucleic acid (shown as the sequence a b c d e) with a completely or partially double-stranded capture probe that contains complementary sequences on the two strands (shown as poly-A and poly-T sequences) and one target-complementary region (shown as the sequence a' b' c' on the poly-T containing strand), to form a capture hybrid made up of the target nucleic acid hybridized to the target-complementary region of the capture probe strand, and another portion of the capture probe strand (poly-T) hybridized to a complementary immobilized probe (shown as poly-A attached to a capture support), followed by releasing the target nucleic acid into solution to form a detection hybrid made up of a detection probe (shown by the sequence a' b' c' d' e') hybridized to the target nucleic acid to produce a detectable signal (shown by the black star icon) to indicate the presence of the target.

"Consisting essentially of" is used to mean that additional component(s), composition(s) or method step(s) that do not materially change the basic and novel characteristics of the present invention may be included in the compositions, kits or methods of the present invention. Such characteristics include the ability of a target-complementary region of an oligomer to bind or hybridize specifically to a target nucleic acid in a sample, the ability of a capture hybrid to be separated from other sample components, and the ability of a detection probe to hybridize to the target nucleic acid and provide a detectable signal to indicate the presence of the target in a sample. These characteristics include the structural features of the capture probes as described herein, which do not rely on any particular sequence as illustrated in FIGS. 1 to 3. It will be appreciated by those skilled in the art that a variety of conditions may be used to create a capture hybrid and a detection hybrid, and further that a variety of devices or systems may be used to accomplish the method steps of the invention. Any component(s), composition(s), or method step(s) that have a material effect on the basic and novel characteristics of the methods of the present invention, as exemplified by the embodiments described herein, would fall outside of this term.

Examples of capture probes are oligomers of DNA, RNA and/or analogs thereof that are comprised of sequences of at least 10 nucleotides complementary to a target nucleic acid. Preferred embodiments include oligomers that contain a target-complementary region of about 20 nucleotides that has 2'-O-methyl linkages or other modified structure to enhance binding. Embodiments of capture probes include oligomers that have a target-complementary sequences of about 15 to 25 nucleotides covalently attached to a homopolymer sequence at the 3' and/or 5' regions of the capture probe. Some embodiments include a poly-dA sequence of about 15 to 30 nucleotides covalently attached to one end of the target-complementary region of the capture probe.

Some capture probe embodiments include an oligomer that contains a 5' region, a middle target-complementary region, and a 3' region, that can be diagrammed as: 5' $X_n$ a' b' c' $Y_n$ 3', in which $X_n$ indicates sequence X that comprises n residues, a' b' c' indicates the target-complementary sequence, and $Y_n$ indicates sequence Y that comprises n residues, in which the $X_n$ and $Y_n$ regions can form a double-stranded structure so that the entire capture probe forms a hairpin structure with the target-complementary sequence as the loop. Some embodiments include complementary homopolymeric sequences at the 5' $X_n$ and 3' $Y_n$ regions that flank the target-complementary region of the linear capture probe so that under hybridizing conditions it forms a partially double-stranded hairpin structure by intramolecular hybridization of the homopolymeric sequences. Examples of hairpin capture probes include a 5' poly-dT region adjacent to the target-complementary region and a 3' poly-dA region so that the target-complementary region forms the loop of the hairpin structure when the poly-dT and poly-dA regions are bound to each other, as illustrated in FIG. 2. In this embodiment, the target-complementary region remains substantially single-stranded in the hairpin structure. Those skilled in the art will understand that any complementary sequences located in the 5' and 3' regions may be used to flank the target-complementary region in an oligomer that forms a hairpin capture probe structure.

Other capture probe embodiments include partially or completely double-stranded structures made up of two oligomer strands in which at least a portion of each of the individual single strands is complementary to a portion of the opposing single strand. Such embodiments can be diagramed as:

```
(first strand)     5' X.sub.n a' b' c' 3'
(second strand)    3' Y.sub.n a  b  c  5'
``` in which $X_n$ indicates sequence X that comprises n residues, a' b' c' indicates the target-complementary sequence, a b c indicates an optional sequence complementary to the target-complementary sequence, and $Y_n$ indicates sequence Y that comprises n residues, in which the $X_n$ and $Y_n$ regions can form a double-stranded structure. For example, a first single strand contains a 5' poly-dT portion for $X_n$ covalently linked to a 3' target-complementary region, and a second single strand contains a 3' poly-dA portion for $Y_n$ covalently linked to another 5' sequence region which may be complementary to a portion of the first strand, where the double-stranded structure is made up of at least the hybridized poly-dT/poly-dA regions. Such a capture probe is illustrated in FIG. 3.

Other embodiments of capture probes are single-stranded oligomers made up of a 3' or 5' target-complementary region and a contiguous region that binds to an immobilized probe, which can be diagramed as:

```
5' X.sub.n a' b' c' 3',
or
5' a' b' c' X.sub.n 3'
``` in which $X_n$ indicates sequence X that comprises n residues, and a' b' c' indicates the target-complementary sequence. One such embodiment is illustrated in FIG. 1.

Examples preferred embodiments of detection probes include oligonucleotides of about 5 to 50 nucleotides in length having an attached label that is detected in a homogeneous reaction, e.g., one that uses differential hydrolysis of a label on a bound or unbound probe. Preferred embodiments of detection probes have a nucleotide sequence that is of the same sense as the target-complementary sequence of the capture probe used in the assay. Other preferred embodiments of detection probes include those of the same nucleotide sequence as the target-complementary sequence of the capture probe. Preferred detection probes have an attached chemiluminescent marker, e.g., an acridinium ester (AE)

compound (U.S. Pat. Nos. 5,185,439, 5,639,604, 5,585,481, and 5,656,744). In preferred embodiments, an acridinium ester label is attached to a central region of the probe near a region of A and T base pairs by using a non-nucleotide linker (U.S. Pat. Nos. 5,585,481 and 5,656,744, Arnold, et al.) which restricts the amines of the nucleotide bases on both sides of the AE and provides a site for intercalation. Alternatively, an AE label may be attached to the 3' or 5' terminus of the detection probe which is used in conjunction with a second oligomer that hybridizes adjacent to the detection probe on the target nucleic acid to restrict the effects of nearby amine contributed by the target nucleic acid. Another embodiment attaches an AE label at or near the site of a mismatch with a related non-target polynucleotide sequence, to permit discrimination between the related sequence and the target sequence that may differ by only one nucleotide because the area of the duplex around the mismatch site is sufficiently destabilized to render the AE on the probe hybridized to the related non-target sequence susceptible to hydrolysis degradation.

The methods of the present invention combine the steps of isolating a target nucleic acid from a sample with detecting the target nucleic acid by using a detection probe to produce a detectable signal when the target nucleic acid is present in the sample. Compositions of the invention include the structural capture probes, immobilized probes on capture supports, and detection probes described herein, which may be included in kits with other reagents for performing the methods. The figures illustrate certain embodiments of the invention schematically.

FIG. 1 illustrates a method embodiment that uses a single-stranded capture probe to capture a target nucleic acid from a sample, followed by detection of the target nucleic acid by forming a detection hybrid to produce a detectable signal. The capture probe (shown as a sequence of polyA a' b' c') and target nucleic acid (shown as a sequence of a b c d) are mixed in solution. Those skilled in the art will understand that a double-stranded target nucleic acid may be treated using standard methods to chemically or physically dissociate the strands and make single strands accessible for hybridization with the capture probe. The capture probe includes a target-complementary region (sequence a' b' c') and another portion (polyA) that binds with an immobilized probe (shown as a poly-T attached to a capture support). Those skilled in the art will recognize that any member of a specific binding pair, including other nucleic acid sequences, may be substituted for the illustrated poly-A region, so long as the specific binding pair member of the capture probe binds to the immobilized probe which is or contains the other member of the specific binding pair.

The capture probe forms a capture hybrid by hybridizing the target-complementary region of the probe to the target nucleic acid and hybridizing or otherwise binding to an immobilized probe attached to a capture support. The immobilized probe, shown as a poly-T oligomer attached to the capture support, is complementary to the poly-A portion of the capture probe. The capture hybrid may be formed by simultaneously binding the immobilize probe, capture probe and target nucleic acid, or may be formed in sequential steps. For example, sequential formation of the capture hybrid may first form a complex made up of the capture probe and the target nucleic acid, and then the complex attaches to the solid support by binding a portion of the capture probe to the immobilized probe. Another example of sequential formation first attaches the capture probe to the immobilized probe and then binds the target nucleic acid to the capture probe at its target-complementary region. Following formation of the capture hybrid, the capture hybrid is isolated from other sample components by physically separating the capture support using any of a variety of known methods, e.g., centrifugation, filtration, magnetic attraction of a magnetic capture support. To further facilitate isolation of the target nucleic acid from other sample components that adhere non-specifically to any portion of the capture hybrid, the capture hybrid may be washed one or more times to dilute and remove other sample components. Washing may be accomplished by dissociating the capture hybrid into its individual components in an appropriate aqueous solution (e.g., 10 mM Tris, 1 mM EDTA) and appropriate conditions (e.g., temperature above the Tm of the components) and then readjusting the conditions to permit reformation of the capture hybrid. For ease of handling and minimization of steps, washing preferably rinses the intact capture hybrid attached to the capture support in a solution by using conditions that maintain the capture hybrid.

Next, the target is released from the capture hybrid. For example, the capture hybrid is released into its individual components to free the target nucleic acid into solution which makes it available to form a detectable complex with a detection probe. As illustrated, the capture probe oligomer is released into solution but will not hybridize to the detection probe because the capture and detection probe oligomers are strands of the same sense. A detection probe (shown as a' b' c' d') is provided in appropriate conditions to hybridize with the target nucleic acid (shown as a b c d), thus forming a detection hybrid. Because the released capture probe may compete with the detection probe for hybridization to the target nucleic acid, those skilled in the art will appreciate that the detection probe should be provided in excess or exhibit higher affinity (compared to the capture probe) for the target nucleic acid by virtue of the detection. probe's length and/or structural modifications (e.g., backbone). As illustrated the detection probe has a longer target-complementary sequence than the capture probe's target-complementary sequence. The target nucleic acid is illustrated as approximately the same length as the detection probe, but those skilled in the art will recognize that the detection probe may be shorter than the target nucleic acid and bind to a target region which differs from the target region recognized by a capture probe. Optionally, one or more additional oligomers may bind to the target nucleic acid in the detection step to facilitate binding the detection probe and/or producing a detectable signal. Such additional oligomers include, e.g., helpers, competitive probes for cross-reacting non-target sequences, or an oligomer that brings another component used in signal production (e.g., enzyme, substrate, catalyst, or energy emitter) into proximity with the detection probe (U.S. Pat. Nos. 5,030,557, Hogan et al.; 5,434,047, Arnold; and 5,928,862, Morrison). The detection step uses conditions appropriate for production of a detectable signal (shown as a black star) from the detection hybrid, using methods well known in the art. Detection of a signal from the detection hybrid indicates the presence of the target nucleic acid in the sample.

FIG. 2 illustrates another method embodiment which uses similar steps to those illustrated in FIG. 1, but uses a capture probe that forms a hairpin structure, which is partially double-stranded and contains a single-stranded loop region that includes the target-complementary region. The capture probe includes complementary 5' and 3' sequences (shown as poly-T and poly-A), which form the double-stranded portion of the hairpin, flanking the target-complementary region (shown as a' b' c' d'), which forms the loop. In this embodiment, the 5' and 3' ends of the hairpin capture probe are separated (e.g., heating above the Tm to dissociate the hydrogen bonds) to make a linear single-stranded capture probe before hybridization with the target nucleic acid (shown as sequence d c b a). A double-stranded target in the sample may also be melted in a single melting step that linearizes the capture probe and dissociates that target nucleic acid strands before hybridization of the capture probe and the target strand. Alternatively, hybridization of the target-complementary region with the target may occur (e.g., by strand displacement or strand invasion) without a melting step, thus separating the 5' and 3' ends of the capture probe. Excess capture probes that do not hybridize to the target would reform the hairpin structure by intramolecular hybridization to effectively prevent binding of the capture probe to other components in the mixture, such as the immobilized probe.

In this embodiment, the capture hybrid is made up of the target nucleic acid hybridized to the target-complementary region of the capture probe and one end of the capture probe hybridized to a complementary immobilized probe. As illustrated, a 3' poly-A region of the capture probe hybridizes to an immobilized probe of poly-T attached to the capture support. Then, the solution phase is separated from the capture hybrids attached to the capture support and optional washing step(s) may be used to further remove sample components, including excess hairpin capture probes unbound to the target. The method proceeds as described above for FIG. 1, by releasing the target from the capture hybrid or separating the capture hybrid into its components, and then forming a detection hybrid made up of a detection probe (shown as sequence a' b' c' d') hybridized specifically to the target nucleic acid. As illustrated, the capture probe released from the capture hybrid reforms the hairpin structure and will not hybridize to the immobilized probe because of the preferred intramolecular hybridization or the detection probe because it is the same sense strand as the detection probe. This is an advantage of this embodiment because it prevents or minimizes competition between the capture probe and the detection probe for binding to the target. The detection hybrid made up of the detection probe and the target produces a detectable signal (shown as a black star) to indicate the presence of the target in the sample.

FIG. 3 illustrates a method embodiment in which the target nucleic acid is captured by using a completely or partially double-stranded capture probe that contains complementary sequences on two strands (shown as a 3' poly-A region on one strand and a 5' poly-T region on the other strand) and at least one target-complementary region (shown as a' b' c' on the poly-T containing strand). In this embodiment, only one strand of the capture probe hybridizes to the target nucleic acid (shown as sequence a b c d e). It is important that the capture probe strand that binds to the target sequence also contains a specific binding partner member that binds to the immobilized probe (shown as a poly-A strand on the capture support). The partially double-stranded capture probe is usually dissociated before forming the capture hybrid although strand displacement caused by the target binding to the target-complementary region of the capture probe may separate the capture probe strands. FIG. 3 illustrates a completely double-stranded embodiment in which the two strands contain portions that are complementary to each other (shown as poly-A on one strand, and poly-T on the other strand), and one strand contains a target-complementary sequence whereas the other strand contain a sequence complementary to the target-complementary sequence. Those skilled in the art will appreciate that the capture probe may be partially double-stranded (e.g., substituting a polyA strand for the polyA-a b c strand shown in FIG. 3). For completely and partially double-stranded capture probes, the same assay steps are used, optionally starting with separation of the capture probe strands using standard methods to allow hybridization of the target-complementary portion of one capture probe strand to the target nucleic acid. Because the two capture probe strands can rehybridize (e.g., via poly-A binding to polyT) and interfere with the target-complementary sequence of the capture probe strand binding to the target nucleic acid, those skilled in the art will appreciate that the capture probe may be synthesized with modifications to optimize hybridization to the target nucleic acid.

In this embodiment, the capture hybrid is made up of the target nucleic acid hybridized to the target-complementary region of one capture probe strand, and another portion of the same capture probe strand (shown as poly-T) is bound to an immobilized probe (shown as poly-A) attached to a capture support. As described above, the capture hybrid attached to the support is separated from other sample components and, optionally, washed to remove sample components and capture probe strands unbound to the capture hybrid. Capture probe strands that do not bind to the target sequence can reform the partially or completely double-stranded structure and be washed away, along with unbound single strands. Then, the target nucleic acid is released from the capture hybrid or the capture hybrid is separated into its components, and the released target is bound in solution by a detection probe (shown as sequence a' b' c' d' e') to form a detection hybrid that produces a signal (shown as a black star) which is detected to indicate the presence of the target nucleic acid in the sample. The released capture probe strand from the capture hybrid remains in solution as illustrated in FIG. 3, but does not bind the detection probe because it is the same sense strand as the detection probe. Those skilled in the art will appreciate that the detection probe should include structure that favors its binding to the target nucleic acid (e.g., increased sequence length and/or backbone modifications) to minimize competition between the detection probe and the released capture probe strand for binding to the target.

A typical assay that uses a method described herein involves providing a sample containing a nucleic acid of interest. Such a sample may be used directly in the assay or prepared by using any of a variety of methods, from simple dilution of a biological fluid with a lysing solution to more complex methods that are well known in the art (e.g., Su et al., *J. Mol. Diagn.* 2004, 6:101-107; Sambrook, J. et al., 1989, *Molecular Cloning, A Laboratory Manual*, $2^{nd}$ ed., pp. 7.37-7.57; and U.S. Pat. Nos. 5,374,522, 5,386,024, 5,786,208, 5,837,452, and 6,551,778). Typically, a sample containing a target nucleic acid is heated to inactivate enzymes in the sample and to make the nucleic acids in the sample single-stranded (e.g., 90-100.deg.C. for 2-10 min, then rapidly cooling to 0-5.deg.C.). To form a capture hybrid, the sample is incubated in appropriate hybridization conditions with a capture probe (e.g., any of the forms described above) and an immobilized probe attached to a capture support. An efficient method mixes these components together in a hybridization mixture and uses first conditions to promote hybridization between the target-complementary region of a capture probe strand and the target nucleic acid, followed by second conditions to promote binding of the capture probe:target complex to the immobilized probe. For example, the first conditions may incubate the mixture at a temperature below the Tm for the target-complementary sequence of the capture probe and the target sequence but above the Tm for hybridization of sequences that bind the capture probe and the immobilized probe, followed by incubating at a second temperature below the Tm for the capture probe binding to immobilized probe sequences (U.S. Pat. No. 6,110,678). In embodiments in which the capture hybrid is attached to the capture support by using members of a specific binding pair that do not require nucleic acid hybridization (e.g., biotin and avidin or streptavidin), appropriate conditions for the selected binding pair members are used. Following formation of the capture hybrids, the capture hybrids attached to the capture support are separated physically from other sample components by using well known methods appropriate for the support, e.g., removing a filter, membrane, or particles from the solution phase by using filtration, centrifugation, gravity, magnetic force, and the like. When the capture support with attached capture hybrids have been separated from other sample components, optional washing steps may be included to further purify the captured target nucleic acid, preferably performed while maintaining the capture hybrid attached to the capture support. Then the target nucleic acid or all components of the capture hybrid are released into solution to free the target for the detection step. Release of the target or capture hybrid components may be performed by any known method, such as, e.g., changing the temperature or chemical composition of the mixture to promote dissociation of the capture hybrid into one or more of its nucleic acid components. Typically, a simple heating step is performed to melt the target and capture probe strands, e.g., in an aqueous solution of low ionic strength, at 90-100.deg.C. for 5 min, followed by rapid cooling to 0-5.deg.C. Other components of the capture hybrid may be released (e.g., capture probe), but only the target nucleic acid must be made available to bind to the detection probe. The soluble phase containing the released target nucleic acid may be separated from other components of the mixture (e.g., capture support and/or unbound capture probes) but this is not critical because the capture probe strand is of the same sense as the detection probe and, therefore, will not interfere with the detection probe binding to the target. As illustrated in FIG. 2, some embodiments further sequester the capture probe by reforming via intramolecular hybridization the hairpin form of the capture probes. The detection step may be performed in soluble phase by adding a detection probe directly to the soluble phase containing the released target nucleic acid and incubating the mixture in hybridization conditions suitable for binding the detection probe and target sequences (e.g., adding salts to the soluble phase to make a solution of suitable ionic strength and incubating at 25-60.deg.C.). After the detection probe binds to the target nucleic acid to form the detection hybrid, a signal from the hybrid is detected to indicate the presence of the target in the tested sample. Routine procedures may be used to remove unbound detection probe before signal detection. In a preferred embodiment, the signal from the detection hybrid is detected in a homogeneous reaction to avoid having to separate the unbound probes before signal detection from the bound probes (e.g., as described in U.S. Pat. Nos. 5,283,174, 5,639,604, 5,948,899, 5,658,737, 5,756,709, 5,827,656, and 5,840,873). Conditions suitable for producing and detecting a signal from the chosen label in the detection hybrid are well known to those of ordinary skill in the art.

The invention also includes kits containing components for performing the methods for detecting target nucleic acids described herein. Preferred kits contain at least one detection probe specific for the target nucleic acid and a means for forming a capture hybrid containing the target nucleic acid. Exemplary kits include a single-stranded capture probe containing a target-complementary region and a means for binding to an immobilized probe, with a detection probe specific for the target. Other exemplary kits include a capture probe containing a target-complementary region flanked by two complementary regions that form a hairpin structure under hybridization conditions, where one of the complementary regions serves as a means for binding the capture probe to an immobilized probe, with a target-specific detection probe. Another exemplary kit includes a completely or partially double-stranded capture probe containing in one strand a target-complementary region and a means for binding to an immobilized probe, with a target-specific detection probe. Exemplary kits may further contain one or more immobilized probes attached to a capture support, where the immobilized probe is capable of binding to a portion of the capture probe(s) in the kit, such as by containing a complementary nucleotide sequence to a portion of the capture probe(s) or by containing a member of a specific binding pair (e.g., avidin) that binds to its other binding pair member on the capture probe (e.g., biotin). In preferred kits, the capture support is a magnetized particle, preferably a paramagnetic bead, with homopolymeric oligomers (e.g., polyA, polyT, polyC, or polyG) attached to it that are complementary to a homopolymeric portion of the capture probe in the kit. Kit embodiments may also contain chemical compounds used in forming the capture hybrid and/or detection hybrid, such as salts, buffers, chelating agents, and other inorganic or organic compounds. Kit embodiments may contain chemical compounds used in releasing the target nucleic acid from a capture hybrid, such as salts, buffers, chelating agents, denaturants, and other inorganic or organic compounds. Kit embodiments may contain chemical compounds used in the detection step, such as enzymes, substrates, acids or bases to adjust pH of a mixture, salts, buffers, chelating agents, and other inorganic or organic compounds used in producing a detectable signal from a detection hybrid. Kit embodiments may also contain chemicals for preparing samples for use in the invention methods which may include individual components or mixtures of lysing agents for disrupting tissue or cellular material and preserving the integrity of nucleic acids. Such compositions include enzymes, detergents, chaotropic agents, chelating agents, salts, buffering agents, and other inorganic or organic compounds. Kits may include any combination of the capture probe, detection probe, and immobilize probe components described above which are packaged in combination with each other, either as a mixture or in individual containers. It will be clear to skilled artisans that the invention includes many different kit configurations.

Aspects and embodiments of the present invention are illustrated in the Examples that follow. Methods and reagents for nucleic acid synthesis, hybridization, and detection of labels were used substantially as described herein, although those skilled in the art will appreciate that other routine methods and standard reagents may also be used to achieve equivalent results. Oligonucleotides were synthesized using standard phosphoramidite chemistry (Caruthers of al., 1987, Methods in Enzymol., 154: 287), purified using routine chromatographic methods (e.g., HPLC), and typically stored in a solution of 10 mM Tris, 1 mM EDTA (pH 7.5), at room temperature to −80.deg.C. In the target capture steps illustrated in the examples, magnetic particles were used as the capture support which were separated from the soluble phase by applying a magnetic field to the outside of the assay container, although those skilled in the art will appreciate that other means of separation may be used. The supernatant containing soluble components was removed, and the hybridization complexes bound to the particles were washed (one to three times with a washing solution of sufficient ionic strength to maintain bonds binding the captured hybrid to the magnetic particles at the washing temperature, usually about 25.deg.C.). Washing generally is performed at room temperature by suspending the particles in the washing solution, separating particles, and removing the supernatant, and repeating those steps for each wash. For the detection step, the detection probe was incubated with the released target nucleic acid in an aqueous solution containing appropriate salts and buffers at a temperature below the Tm predicted for the detection probe sequence and its target sequence, usually for 30-60 min. When an AE-labeled detection probe was used, a homogeneous detection step was performed which uses differential hydrolysis of the AE label on unbound probes compared to AE-labeled probes bound to the target (described in detail in U.S. Pat. No. 5,283,174). For example, hydrolysis was performed by adding a selection reagent that promotes hydrolysis of the AE label on unbound probes (e.g., a basic solution), followed by adding a detection reagent that catalyzes chemiluminescence from AE attached to bound probes (e.g., $H_2O_2$), and the chemiluminescent signal (referred to as relative light units or RLU) was detected on a luminometer (e.g., LEADER® 450HC+, Gen-Probe Incorporated, San Diego, Calif.).

The following examples describe some preferred embodiments and reagents used in these assays. The skilled artisan will appreciate that other reagents and conditions may be substituted for those described herein to perform the method steps. For example, the reagents and conditions for producing and detecting a signal will be selected by the skilled artisan based on the chosen detection probe label. Those skilled in the art will understand that the invention methods may be performed using any chosen target nucleic acid sequence that can hybridize to a complementary sequence, i.e., the method is not dependent on any particular probe or target sequences. One of ordinary skill in the art will be able to select the target sequence and then design and synthesize the appropriate target-complementary sequence of any of the capture probe forms described herein, and a target-specific detection probe by using routine methods. That is, specific assays will rely on selection of a target sequence and the appropriate target-complementary sequences contained in the capture and detection probes that include the structural characteristics described herein, and such selection can be performed by one of ordinary skill in the art using standard procedures, followed by routine testing of the designed components to optimize detection of the selected target by using the methods described herein.

EXAMPLE 1

Detection of Different Labeled Probes

To design detection probes, a target sequence of 23 nt was selected from a sequence common to genomic sequences of human Herpesvirus 5 (Cytomegalovirus) strains (Dunn et al., 2003, *Proc. Natl. Acad. Sci. USA* 100(24): 14223-14228; GenBank accession nos. AC146999, AC146851, and AY315197) and complementary to portions of fluorescent protein genes (GenBank accession nos. AY 303166, AY303167, and AY237157). Oligomers of 23 nt that were completely complementary to the target sequence were synthesized in vitro as a 2'-O-methyl oligoribonucleotides which had 52% GC content. Three versions of the probes were labeled with a linker at different positions (between bases 8 and 9, 12 and 13, and 13 and 14 of the 23-mer) and an AE label attached at the linker by using methods previously described in detail (U.S. Pat. Nos. 5,185,439, 5,283,174, and 5,656,744). The labeled probes (0.1 μmol per reaction) were individually hybridized at 60.deg.C. for 1 hr to a complementary synthetic ssRNA target sequence (10 μmol per reaction) in a 30 μl reaction mixture containing 15 μl of a hybridization reagent (190 mM succinate, 17% (w/v) lithium lauryl sulfate (LLS), 100 mM LiOH, 3 mM EDTA, and 3 mM EGTA, at pH 5.1). Then the hybridization mixture was diluted to 500 μl with the hybridization reagent and 20 μl aliquots were removed for performing the detection step by adding to each detection reaction mixture 80 μl of the hybridization reagent, and then 200 μl of a selection reagent (600 mM boric acid, 182.5 mM NaOH, 1% (v/v) octoxynol (TRITON® X-100), at pH 8.5), and hydrolysis was performed at 50.deg.C. for varying periods of time. Then, production and detection of the signal was performed by adding 200 μl of a detection reagent (1 mM nitric acid and 32 mM $H_2O_2$) followed by adding 200 μl of 1.5 M NaOH and the chemiluminescent signal (RLU) was measured (for 2 sec) by using a luminometer. The same detection reaction method was performed on aliquots that contained the individual probes without the ssRNA target to measure hydrolysis of the AE label on unbound probes. From these results, the time at which half of the detectable label for each probe composition was hydrolyzed ($T_{1/2}$), when the complementary target strand was present or absent, was determined. The $T_{1/2}$ for all three probes without the target (i.e., unbound probes) was between 0.69 and 1.05 min, whereas when the target was present (i.e., bound probes) the $T_{1/2}$ was between 25.8 and 125 min, indicating that the detection probes bound to the target and produced a detectable signal in excess of the background signal in a homogeneous reaction mixture. When probes were hybridized with the target, they exhibited different $T_{1/2}$ characteristics: the probe labeled between positions 12 and 13 had the shortest $T_{1/2}$ (25.8 min), the probe labeled between positions 13 and 14 had the longest $T_{1/2}$ (125 min), and the probe labeled between positions 8 and 9 was an intermediate $T_{1/2}$ (69 min). These results show that all three probes were capable of binding to the complementary RNA target, that labels in unbound probes could be distinguished from labels in bound probes by differential hydrolysis characteristics, and that the labeling position on the oligomer affected the rate of label hydrolysis so that optimal probes for an assay may be selected and designed using routine testing.

EXAMPLE 2

Sensitivity of Detection of Single-stranded and Double-stranded Targets

The sensitivity of target detection was determined by using the same target and detection probe sequences as in Example 1, but comparing detection of the RNA target when it was in ssRNA or dsRNA form. The ssRNA target oligomer and detection probe oligomer labeled with AE between positions 13 and 14 were used as in Example 1. In these assays, all reactions contained 0.1 μmol of the AE-labeled probe which was hybridized to the ssRNA target present in a range of 0 to 5 fmol per hybridization reaction (100 μl hybridization mixtures incubated at 60.deg.C. for 1 hr). Following hybridization, the AE label on unbound probe was hydrolyzed by adding 200 μl of the selection reagent and incubating at 50.deg.C. for 10 min, and then the chemiluminescent signal from bound probe was detected substantially as described in Example 1. Results shown in Table 1, columns 1 and 2, demonstrate that a linear detectable signal was measured over the range of target amounts tested. As little as 0.005 fmol of the ssRNA target in the reaction resulted in a detectable signal over the background signal obtained when no target nucleic acid was present in the assay. "Net RLU" data (column 2) was calculated by subtracting the background RLU (560 RLU when no target was present) from the detected RLU for each test sample.

In the tests performed using the dsRNA target, the target was made by synthesizing a complementary RNA strand to the ssRNA target oligomer described above and hybridizing the two complementary RNA strands together. The dsRNA target was tested substantially as described above by using the same probe as described above synthesized as a 2'-O-methyl oligoribonucleotide and labeled with AE between positions 13 and 14. This detection probe was complementary to one of the strands in the dsRNA target. Before hybridization with the AE-labeled probe, the dsRNA target was denatured by heating it in solution (10 mM Li-succinate and 0.01% LLS, pH5.0) at 90.deg.C. for 5-7 min, followed by quickly cooling on ice. In Test 1, 50 μmol of the target dsRNA was denatured and then diluted to make the different amounts of target used in each of the 100 μl hybridization reactions. In Test 2, the appropriate amounts of the target dsRNA were distributed to separate tubes in 50 μl aliquots, heat denatured as described above, and then 50 μl of the hybridization reagent containing the labeled probe was added to each tube make the hybridization reaction mixtures. The hybridization and detection reactions were performed substantially as described above for the ssRNA target reactions and the results for the dsRNA target are shown in Table 1, columns 3 to 5. The background signal detected when no target was present (942 RLU in Test 1, 932 RLU in Test 2) was subtracted from the detected signal when the dsRNA target was present to obtain the "Net RLU" (column 4 for Test 1, and column 5 for Test 2). The Net RLU measurements showed that the assay produced a detectable signal that was a substantially linear response over the range of target amounts tested. A positive signal was detected when as little as 0.01 fmol (Test 1) to 0.05 fmol (Test 2) of the target RNA was present in the reaction indicating the sensitivity of the detection step.

TABLE 1

Signal Measured for Hybridization Reactions Containing Different Amounts of Target

| ssRNA (fmol) | Net RLU | dsRNA (fmol) | Net RLU-Test 1 | Net RLU-Test 2 |
|---|---|---|---|---|
| 0.005 | 391 | — | — | — |
| 0.01 | 719 | 0.01 | 122 | — |
| 0.02 | 1,289 | 0.02 | 151 | — |
| 0.05 | 3,376 | 0.05 | 625 | 2,796 |
| 0.07 | 4,648 | 0.07 | 567 | — |
| 0.1 | 7,157 | 0.1 | 1,066 | 5,561 |
| 0.25 | 16,922 | 0.25 | 2,079 | — |
| 0.5 | 29,729 | 0.5 | 4,443 | 27,142 |
| 1.0 | 64,929 | 1.0 | 7,974 | — |
| 5.0 | 287,821 | 5.0 | 54,077 | 240,787 |

EXAMPLE 3

Capture and Detection of a Target RNA

In these assays, a capture probe capable of forming a hairpin structure under hybridization conditions was used to capture a target nucleic acid from a sample, followed by hybridization of the target nucleic acid with a labeled detection probe and detection of a signal from bound detection probe. The capture probes used in these experiments all contain structural features that allow formation of a hairpin structure: a 5' region homopolymeric sequence, a 3' region sequence that was fully or partially complementary to the 5' region sequence, and a target-complementary sequence flanked by the 5' and 3' region sequences. The 5' and 3' region sequences form the "stem" portion of the hairpin structure, and the target-complementary sequence forms the "loop" portion of the hairpin structure.

Three versions of a hairpin capture probe were synthesized and assayed using routine methods to determine the Tm of the stem of the hairpin capture probe. The complementary 5' and 3' region sequences of all three probes were synthesized with deoxyribonucleotide linkages. The target-complementary sequence of each of the hairpin probes was the 23-nt target-complementary sequence as in Example 1, synthesized in probes 1 and 2 with 2'-O-methyl linkages and in probe 3 with deoxyribonucleotide linkages. In probes 1 and 3, the 5' region was a $(dT)_{.sub.12}$ sequence and the 3' region was a $(dA)_{.sub.12}$ sequence; and in probe 2, the 5' region sequence was $(dT)_{.sub.5}A(dT)_{.sub.6}$ which is partially complementary to the 3' region sequence of $(dA)_{.sub.12}$. Schematically, the resulting capture probe sequences were as shown in linear form below:

```
                          (probes 1 and 3; SEQ ID NO: 1)
  5' TTTTTTTTTTTT - N.sub.23 - AAAAAAAAAAAA 3',
  and (probe 2; SEQ ID NO: 2)
  5' TTTTTATTTTTT - N.sub.23 - AAAAAAAAAAAA 3',
``` in which N.sub.23 represents the target-complementary sequence. In will readily be appreciated that these linear sequences form partially double-stranded hairpin structures by intramolecular hybridization of the 5' region to the 3' region and the target-complementary sequence (N.sub.23) becomes the loop portion of the hairpin structure. The Tm's for the double-stranded stem portions of these hairpin probes were in a range of about 46.deg.C. to about 57.deg.C. (46.3.deg.C. for probe 2, 55.7.deg.C. for probe 3, and 56.7.deg.C. for probe 1).

Capture using these hairpin capture probes and detection of the target was performed using the dsRNA target and AE-labeled probe described in Example 2, using target amounts ranging from 0.05 to 5 fmol per reaction. To provide a sample similar to a clinical sample, the dsRNA target present in 200 μl of sample transport solution (110 mM LLS, 15 mM sodium phosphate monobasic, 15 mM sodium phosphate dibasic, 1 mM EDTA, 1 mM EGTA, pH 6.7) was mixed with 200 μl of urine, to make a final sample volume of 400 μl. This mixture was heated to denature the dsRNA target (at 90.deg.C. for 5 min, then cooled on ice), to provide a ssRNA target strand for hybridization with the capture probes. For each of the hairpin capture probes tested individually, the denatured RNA target sample was mixed with 100 μl of a target capture reagent (250 mM HEPES, 310 mM LiOH, 1.88 M LiCl, 100 mM EDTA, pH 6.4) containing 0.3 μmol of the hairpin capture probe and 50 μg of magnetic particles which were the capture support (1 micron SERA-MAG.SUP.TM MG-CM particles, Seradyn, Inc. Indianapolis, Ind.), to which immobilized probe oligomers of $dT_{.sub.14}$ were covalently attached. The mixture was incubated at 65.deg.C. for 60 min (a temperature above the Tm of each of the capture probes) and then at room temperature for 30 min to form capture hybrids attached to the particles. Then, the particles with the attached capture hybrids were separated magnetically from the liquid sample components which were removed. The particles with attached capture hybrids were washed twice at room temperature with 500 μl of the sample transport solution and then the particles with attached capture hybrids were separated from the solution which was removed. The washed particles with the attached capture hybrids were mixed with 100 µl of water and heated (90.deg.C. for 5 min) to release the nucleic acid components of the capture hybrids (target and capture probe oligomers released into solution and the immobilized probe remained covalently attached to the capture support particle). For detection of the target, the solution then was mixed with an AE-labeled detection probe, as described in Example 2, in 100 µl of the hybridization reagent and the mixture was incubated under hybridization conditions (55.deg.C. for 60 min) to allow the detection probe to bind to the target strands. Under these conditions, the released capture probes may reform the partially double-stranded hairpin structure by intramolecular hybridization to minimize competitive inhibition caused by the capture probes competing with the detection probes for hybridization to the target strand. The detection probe and the target-complementary sequence of the hairpin capture probes will not hybridize to each other because they are the same sense strands. Detection of the signal from bound detection probes was performed substantially as described in Example 1. Control reactions without target were treated identically and the background signal for all reactions was in the range of 535 to 715 RLU. The experimental results of these assays are shown in Table 2, column 2, as net RLU (detected RLU minus background RLU). For each assay, the ratio of the detected signal to background RLU is shown in Table 2, column 3.

TABLE 2

Assays Performed Using a Hairpin Capture Probe and Detection Probe

| Target Amount (fmol) | Net RLU | Signal/Background Ratio |
|---|---|---|
| 0.05 | 1,248 | 3 |
| 0.1 | 2,223 | 4.4 |
| 0.15 | 3,318 | 6.6 |
| 0.2 | 5,418 | 9 |
| 0.5 | 11,156 | 22 |
| 1.0 | 24,758 | 36 |
| 2.0 | 38,351 | 55 |
| 5.0 | 98,180 | 140 |

The results of these assays show that the combination of capture of a target nucleic acid by using a hairpin capture probe and detection by using a detection probe complementary to one strand of a dsRNA target effectively detected the target present in a sample for all of the amounts of target tested.

EXAMPLE 4

Assays Comparing Different Forms of Capture Probes

These assays compared the relative efficiency of capture and detection of a target sequence, using methods similar to those described in Example 3, when the target capture step was performed by using a capture probe of either a hairpin structure or linear structure. Unless otherwise stated, the reagents used in these tests were the same as disclosed in Examples 1 to 3 above. All of the assays used test samples containing 1 fmol of the ssRNA target, as described in Example 2, in 200 µl of urine mixed with 200 µl of sample transport solution. For the target capture step, each 400 µl test sample was mixed with 100 µl of target capture reagent containing different amounts (0.1, 0.5, 1.0, 2.0, 5.0, 10 and 20 pmoles) of either a partially double-stranded hairpin capture probe as described in Example 3 (SEQ ID NO:1) or a linear single-stranded capture probe of the following structure:

(SEQ ID NO: 3)
5' X N.sub.23 TTTAAAAAAAAAAAA 3' that has substantially the same target-complementary sequence ($N_{23}$) as in the hairpin capture probe, but includes one additional 5' nucleotide (X). In both the hairpin and linear forms of the capture probes, the target-complementary regions were synthesized with 2'-O-methyl linkages. In the hairpin capture probe, the target-complementary region was flanked by the complementary 5' poly-dT and 3' poly-dA regions, whereas in the linear form the target-complementary region was covalently linked to a 3' (dT).sub.3(dA).sub.30 sequence. The reaction mixtures were incubated at 65.deg.C. for 60 min and then at room temperature for 30 min to allow formation of capture hybrids and attachment to the capture support via the immobilized probe. The supports with attached capture hybrids were separated from the liquid sample components by applying a magnetic field and then the supports were washed twice (using 0.5 ml of sample transport solution each) substantially as is described in Example 3. The final wash solution was removed and the capture supports with attached capture hybrids were mixed with 100 µl of water per assay, incubated at 90.deg.C. for 5 min and rapidly cooled on ice to release the capture hybrids into the nucleic acid components before hybridization of the target strand with the detection probe. Then, each test sample was mixed with 0.1 pmole of the AE-labeled detection probe of Example 2 in 100 µl of hybridization reagent and incubated at 55.deg.C. for 60 min to allow hybridization of the detection probe to the target strand. Detection of the chemiluminescent signal from detection probes bound to the target strands was performed substantially as described in Example 3 (add 200 µl of selection reagent, incubate at 55.deg.C. for 10 min, mix with 200 µl of detection reagent and measure chemiluminescence (for 5 sec) on a luminometer). The results are shown in Table 3, as net RLU in column 2 and 3, and the relative percentage of detection obtained when the capture step had been performed by using the linear or hairpin forms of the capture probes, in columns 4 and 5. The net RLU was calculated by subtracting the background RLU from the RLU detected in positive samples (background was 762 RLU for the hairpin probe tests and 749 RLU for the linear probe tests). The relative percentage of detection was calculated by setting the highest detected net RLU at 100% (results for 0.1 pmole of hairpin capture probe) and dividing the lesser net RLU detected in the other tests by the highest net RLU (21,778).

TABLE 3

Comparison of Hairpin and Linear Capture Probes

| Capture Probe (pmole) | Net RLU Hairpin Probe | Net RLU Linear Probe | % Detection Hairpin Probe | % Detection Linear Probe |
|---|---|---|---|---|
| 0.1 | 21,778 | 15,849 | 100 | 72.8 |
| 0.5 | 19,614 | 7,286 | 90.1 | 33.5 |
| 1.0 | 18,248 | 4,172 | 83.8 | 19.2 |
| 2.0 | 17,316 | 2,578 | 79.5 | 11.8 |
| 5.0 | 11,889 | 1,137 | 54.6 | 5.2 |
| 10 | 9,778 | 722 | 44.9 | 3.3 |
| 20 | 4,519 | 458 | 20.7 | 2.1 |

These results show that the assays performed by using a linear form and a hairpin form of the capture probes specific for the same target sequence resulted in a detectable signal for all of the assays performed. The relative percentage of detection was consistently higher when the capture probe was in the hairpin form compared to the linear form. The difference in relative percentage of detection ranged from about 10-fold more when the results obtained for the two forms were compared for the highest amounts of capture probes tested (20 pmoles per reaction), to about 2.7-fold when the results obtained for the two forms were compared for the lowest amount of capture probes tested (0.1 pmole per reaction). The differences between the assays that used the hairpin and linear capture probe forms may result from more competitive inhibition when the linear capture probe was used because the released linear form may compete with the detection probe for hybridization to the target sequence during the detection phase of the assay whereas the hairpin form under the same conditions may reform the hairpin structure to limit competition between the target-complementary region of the capture probe and the detection probe for binding the target.

EXAMPLE 5

Assays Using a Partially Double-Stranded Capture Probe

This example describes an embodiment that uses a completely or partially double-stranded capture probe. The capture probe of this embodiment is made up of two completely or partially complementary strands of which one strand includes a target-complementary region that binds to a portion of the target nucleic acid. One version of the capture probe is made up of a first capture probe strand (SEQ ID NO:4) and a second capture probe strand (SEQ ID NO:5) that are synthesized and hybridized together to make a partially double-stranded capture probe bound by hybridization of at least their complementary 3' polyA and 5' polyT sequences as shown below.

```
                                              (SEQ ID NO: 4)
5'TTTTTTTTTTTTTTTAGAGGATGGGTTTTCTAGGGG 3'

(SEQ ID NO: 5)
3'AAAAAAAAAAAAAAATCTCTCTCTCTCTCTCTC 5'
```

The oligomer of SEQ ID NO:4 contains a 5' poly-T region and a 3' sequence complementary to a sequence contained in a human B19 parvovirus genome (GenBank accession no. AY386330); and the oligomer of SEQ ID NO:5 contains a 5' poly-(TC) region and a 3' poly-A region. In another version, the capture probe is completely double stranded and made up of the first capture probe strand (SEQ ID NO:4) hybridized to its complementary strand (SEQ ID NO:6) as shown below.

```
                                              (SEQ ID NO: 4)
5'TTTTTTTTTTTTTTTAGAGGATGGGTTTTCTAGGGG 3'

(SEQ ID NO: 6)
3'AAAAAAAAAAAAAAATCTCCTACCCAAAAGATCCCC 5'
```

In separate assays, about 3.5 pmole of each version of the capture probes is mixed with a 0.5 ml plasma sample containing parvovirus B19 genomic DNA (denatured and, optionally, sheared or enzymatically digested into fragments of about 100 to 1000 nt long) and an equal volume of target capture reagent containing capture support particles with attached poly(A) oligomers as the immobilized probe. That is, the immobilized poly(A) oligomers are complementary to the 5' poly-dT portion of the capture probe oligomer of SEQ ID NO:4. The mixture is incubated (60-65.deg.C., 20-60 min) to allow the capture probes to dissociate into the component oligomers (SEQ ID NO:4 and SEQ ID NO:5, or SEQ ID NO:4 and SEQ ID NO:6), to allow the target-specific portion of SEQ ID NO:4 to hybridize to the complementary sequence in the parvovirus B19 target DNA. Then, the mixture is incubated at a lower temperature (25-30.deg.C., 14-30 min) to allow the complementary homopolymeric sequences of the capture probe and the immobilized probe to hybridize, thereby attaching the target B19 DNA to the magnetic particles in a capture hybrid that includes the capture probe strands of SEQ ID NO:5 hybridized to the complementary sequence in the parvovirus B19 DNA. Particles with the attached capture hybrids are separated from the sample components by applying a magnetic force to the outside of the container and the liquid sample components, including unhybridized capture probe strands, are removed. A washing step is used in which the particles with the attached capture hybrids are suspended in an aqueous solution of sufficient ionic strength the maintain the capture hybrid attached to the capture support, then the particles are separated from the aqueous solution using magnetic force, and the washing solution with any unbound capture probe oligomers and other sample components is removed. For detection of the captured B19 DNA, the particles with the attached capture hybrids are mixed with a hybridization reagent containing detection probe oligomers of SEQ ID NO:7 (0.1-0.5 pmoles per reaction) labeled with a fluorescent label (e.g., fluorescein) and the detection probes are hybridized to a complementary sequence in the captured B19 DNA by incubating the mixture below the Tm of the detection probe but at a temperature above the melting temperature of the polA-polyT duplex, to release the B19 target nucleic acid into the solution phase (e.g., 55.deg.C. for 20-60 min). The mixture is then incubated at a lower temperature (e.g., 25-30.deg.C. for 10-30 min) to allow hybridization complexes made up of the B19 target DNA, detection probe and the poly-dT containing capture probe strand to attached to the poly (A) immobilized probes on the particles. The particles with attached complexes that contain the hybridized detection probes are separated from the solution phase as described above and the solution phase containing unbound detection probes is discarded. The particles with attached complexes are optionally washed, substantially as described above, under conditions that maintain the hybridization complexes on the particles to remove remaining unbound detection probes. Finally, the particles are mixed with a volume of liquid (e.g., 0.5 ml water) and the fluorescence of the mixture is measured using standard fluorometric procedures. A negative control sample, i.e. plasma containing no B19 particles or DNA, is treated identically as described above and the fluorescence that is measured from the negative control sample indicates background signal for the assay. For both the partially and completely double-stranded versions of the capture probe, these assays produce a detectable positive signal for test samples that contain parvovirus B19 nucleic acid that is significantly greater than the background signal that negative control samples produce. Positive signals indicate the presence of the parvovirus B19 target nucleic acid in the samples.

The invention claimed is:

1. A kit for the detection of a target nucleic acid, wherein the kit comprises: a capture probe having the structure 5'-X.sub.n a' b' c' Y.sub.n-3', wherein X and Y each comprise nucleic acid sequences that can form a double stranded portion of a hairpin structure and wherein one of X or Y is a capture sequence further comprising a first member of a specific binding pair and the other of X or Y is a terminal sequence of the hairpin capture probe, and wherein a' b' c' comprises a target-complementary sequence that hybridizes specifically to a target sequence in the target nucleic acid and is flanked by X and Y to thereby form a loop portion of the hairpin structure; and a detection probe that hybridizes specifically to a target sequence that overlaps or is the same as the target sequence hybridized by the target-complementary sequence of the capture probe.

2. The kit of claim 1, wherein the detection probe hybridizes specifically to the same target sequence hybridized by the target-complementary sequence of the capture probe.

3. The kit of claim 1, wherein the detection probe comprises a target-complementary sequence that is a' b' c'.

4. The kit of claim 1 that further includes an immobilized probe attached to a capture support, wherein the immobilized probe includes a second member of a specific binding pair that binds specifically to the capture probe's first member of a specific binding pair.

5. The kit of claim 4, wherein the first and second specific binding pair members are substantially complementary sequences that hybridize the capture probe to the immobilized probe under hybridizing conditions.

6. The kit of claim 5, wherein the first member of the specific binding pair is a sequence from 10 to 30 nucleobases in length and is substantially a poly-A sequence.

7. The kit of claim 5, wherein the second member of the specific binding pair is a sequence from 10 to 30 nucleobases in length and is substantially a poly-A sequence.

8. The kit of claim 1, wherein said target complementary sequence is synthesized with 2'-O-methyl linkages.

9. The kit of claim 1, wherein Y is the capture sequence that forms the first member of the specific binding pair.

10. The kit of claim 9, wherein the capture probe has the structure 5'-X.sub.n a'b'c' poly(A).sub.10-30.

11. A reaction mixture for the detection of a target nucleic acid, wherein the reaction mixture comprises: a capture probe having the structure 5'-X.sub.n a' b' c' Y.sub.n-3', wherein X and Y each comprise nucleic acid sequences that can form a double stranded portion of a hairpin structure and wherein one of X or Y is a capture sequence further comprising a first member of a specific binding pair and the other of X or Y is a terminal sequence of the hairpin capture probe, and wherein a' b' c' comprises a target-complementary sequence that hybridizes specifically to a target sequence in the target nucleic acid and is flanked by X and Y to thereby form a loop portion of the hairpin structure; and a detection probe that hybridizes specifically to a target sequence that overlaps or is the same as the target sequence hybridized by the target-complementary sequence of the capture probe.

12. The reaction mixture of claim 11, wherein the detection probe hybridizes specifically to the same target sequence hybridized by the target-complementary sequence of the capture probe.

13. The reaction mixture of claim 11, wherein the detection probe comprises a target-complementary sequence that is a' b' c'.

14. The reaction mixture of claim 11, wherein the first member of the specific binding pair is a sequence from 10 to 30 nucleobases in length and is substantially a poly-A sequence.

15. The reaction mixture of claim 11, wherein the second member of the specific binding pair is a sequence from 10 to 30 nucleobases in length and is substantially a poly-A sequence.

16. The reaction mixture of claim 11, wherein said target complementary sequence is synthesized with 2'-O-methyl linkages.

17. The reaction mixture of claim 11, wherein Y is the capture sequence that forms the first member of the specific binding pair.

18. The reaction mixture of claim 17, wherein the capture probe has the structure 5'-X.sub.n a'b'c' poly(A).sub.10-30.

19. The reaction mixture of claim 11, wherein the detection probe is labeled with a chemiluminescent compound.

20. The reaction mixture of claim 19, wherein the chemiluminescent compound is an acridinium ester.

21. The reaction mixture of claim 11, wherein the detection probe is labeled with a fluorescent compound.

22. The reaction mixture of claim 21, wherein the detection probe is a molecular torch or a molecular beacon.

23. The reaction mixture of claim 11, wherein the reaction mixture contains the target nucleic acid, and wherein the detection probe is hybridized to the target nucleic acid.

* * * * *

UNITED STATES PATENT AND TRADEMARK OFFICE
CERTIFICATE OF CORRECTION

PATENT NO. : 8,551,766 B2  
APPLICATION NO. : 12/845640  
DATED : October 8, 2013  
INVENTOR(S) : Becker et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 358 days.

Signed and Sealed this  
Twelfth Day of November, 2013

Teresa Stanek Rea  
*Deputy Director of the United States Patent and Trademark Office*